US012582335B2

(12) United States Patent
Challenor et al.

(10) Patent No.: US 12,582,335 B2
(45) Date of Patent: Mar. 24, 2026

(54) DEVICE, SYSTEM AND METHOD FOR MONITORING AN ANALYTE CONCENTRATION IN A FOETUS

(71) Applicant: VitalTrace Pty Ltd, Crawley (AU)

(72) Inventors: Michael Tom Challenor, Crawley (AU); Arjun Siddharth Kaushik, Crawley (AU); Sanandan Sudhir, Gujarat (IN); Akshay Akshay, New Delhi (IN); Sheldon Salvio Napoleon Pinto, Goa (IN)

(73) Assignee: VitalTrace Pty Ltd, Crawley (AU)

( * ) Notice: Subject to any disclaimer, the term of this patent is extended or adjusted under 35 U.S.C. 154(b) by 1074 days.

(21) Appl. No.: 17/250,951

(22) PCT Filed: Oct. 1, 2019

(86) PCT No.: PCT/AU2019/051067
§ 371 (c)(1),
(2) Date: Apr. 1, 2021

(87) PCT Pub. No.: WO2020/069572
PCT Pub. Date: Apr. 9, 2020

(65) Prior Publication Data
US 2021/0315494 A1      Oct. 14, 2021

(30) Foreign Application Priority Data

Oct. 2, 2018    (AU) ................................ 2018903727

(51) Int. Cl.
*A61B 5/145* (2006.01)
*A61B 5/00* (2006.01)
(Continued)

(52) U.S. Cl.
CPC ........ *A61B 5/14546* (2013.01); *A61B 5/0205* (2013.01); *A61B 5/02411* (2013.01);
(Continued)

(58) Field of Classification Search
CPC .............. A61B 5/14546; A61B 5/0205; A61B 5/02411; A61B 5/02444; A61B 5/1482;
(Continued)

(56) References Cited

U.S. PATENT DOCUMENTS 4,281,659 A    8/1981  Farrar
4,320,764 A  *  3/1982  Hon ................... A61B 5/14542
                                                        600/351
(Continued)

FOREIGN PATENT DOCUMENTS

JP          3965464 A    6/2007
JP       2015077321 A    4/2016
(Continued)

OTHER PUBLICATIONS

International Search Report for PCT/AU2019/051067, dated Jan. 15, 2020.
Written Opinion for PCT/AU2019/051067, dated Jan. 15, 2020.

*Primary Examiner* — Matthew Kremer
*Assistant Examiner* — Meghan R Kumar
(74) *Attorney, Agent, or Firm* — David B. Gornish; Eckert Seamans Cherin & Mellott, LLC

(57) ABSTRACT

The present invention relates to a device for monitoring a concentration of an analyte in a foetus. The device comprises a biosensor for electrochemically measuring a concentration of an analyte in the foetus, a protrusion configured to be at least partially inserted into foetal tissue, and a device body supporting the biosensor and the protrusion. The device is configured such that when the device body contacts the surface area of the foetal tissue, the device body can be anchored to the foetal tissue and the protrusion can be inserted into the tissue so that the reactive substance of the biosensor electrochemically reacts with the analyte in the foetal tissue and in response to the electrochemical reaction
(Continued)

the electrode of the biosensor detects an electronic signal, a strength of the electronic signal being indicative of the concentration of the analyte.

10 Claims, 12 Drawing Sheets

(51) Int. Cl.

| | |
|---|---|
| *A61B 5/0205* | (2006.01) |
| *A61B 5/024* | (2006.01) |
| *A61B 5/1482* | (2006.01) |
| *A61B 5/1486* | (2006.01) |

(52) U.S. Cl.

CPC ........ *A61B 5/02444* (2013.01); *A61B 5/1482* (2013.01); *A61B 5/14865* (2013.01); *A61B 5/6882* (2013.01)

(58) Field of Classification Search

CPC . A61B 5/14865; A61B 5/6882; A61B 5/6867; A61B 2503/02; A61B 5/1464; A61B 5/1473; A61B 5/4362

See application file for complete search history.

(56) References Cited

U.S. PATENT DOCUMENTS

| | | | | |
|---|---|---|---|---|
| 4,437,467 | A | * | 3/1984 | Helfer ................ A61B 5/02411 |
| | | | | 600/376 |
| 4,474,569 | A | | 10/1984 | Newkirk |
| 4,686,996 | A | * | 8/1987 | Ulbrich ................ A61B 5/4362 |
| | | | | 600/376 |
| 4,913,151 | A | * | 4/1990 | Harui ................. A61B 5/14542 |
| | | | | 600/313 |
| 5,373,843 | A | | 12/1994 | Quedens |
| 5,680,859 | A | | 10/1997 | Urion et al. |
| 6,058,321 | A | | 5/2000 | Swayze |
| 7,016,716 | B2 | * | 3/2006 | Rall ..................... A61B 5/4362 |
| | | | | 600/338 |
| 2002/0188221 | A1 | * | 12/2002 | Sohrab ............ A61B 5/150503 |
| | | | | 600/573 |
| 2004/0153008 | A1 | | 8/2004 | Sharf et al. |
| 2011/0196214 | A1 | * | 8/2011 | Edmunds .......... A61B 5/15196 |
| | | | | 600/368 |
| 2013/0012362 | A1 | | 1/2013 | Ju et al. |
| 2015/0366493 | A1 | * | 12/2015 | Cremers ............. A61B 5/4362 |
| | | | | 205/264 |
| 2016/0036718 | A1 | | 2/2016 | Shingari et al. |
| 2017/0112428 | A1 | * | 4/2017 | Cremers ........... A61B 5/14546 |

FOREIGN PATENT DOCUMENTS

| | | | |
|---|---|---|---|
| KR | 1020160132750 | A | 11/2016 |
| WO | 2009-142599 | A1 | 11/2009 |

* cited by examiner

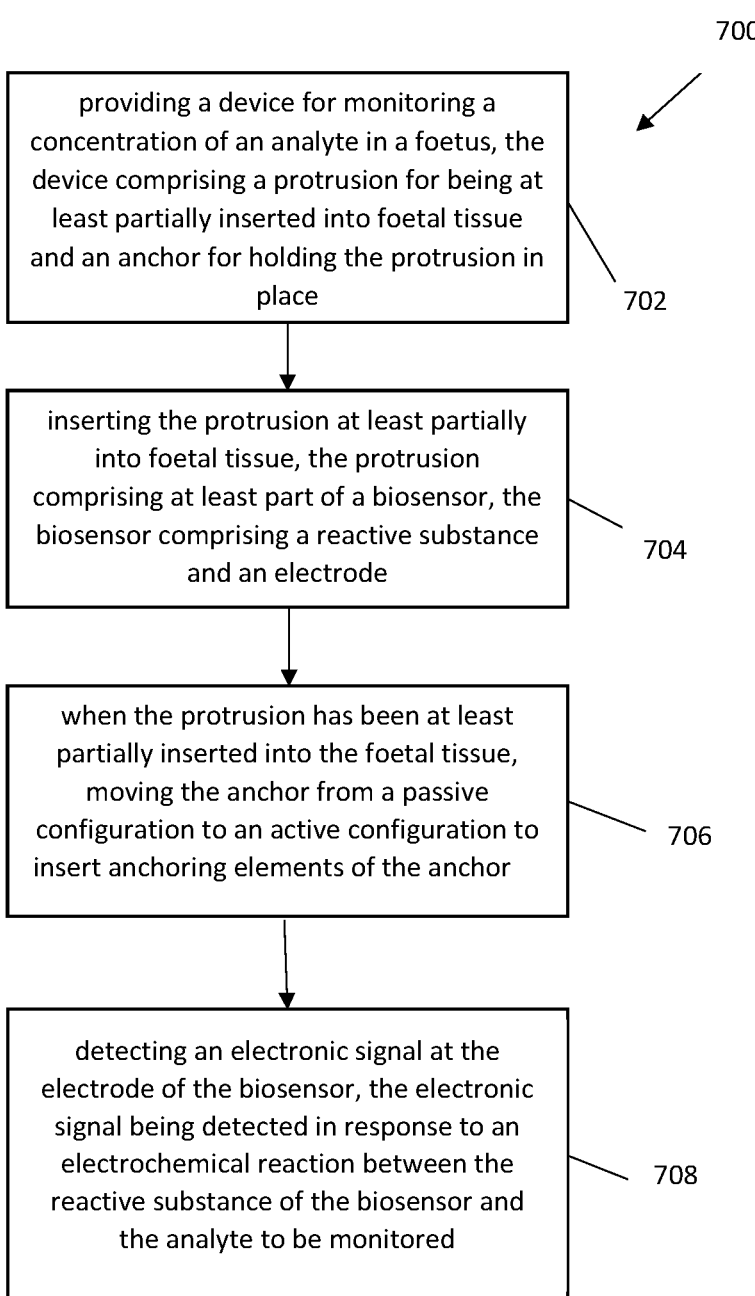

700 providing a device for monitoring a concentration of an analyte in a foetus, the device comprising a protrusion for being at least partially inserted into foetal tissue and an anchor for holding the protrusion in place

702 inserting the protrusion at least partially into foetal tissue, the protrusion comprising at least part of a biosensor, the biosensor comprising a reactive substance and an electrode

704 when the protrusion has been at least partially inserted into the foetal tissue, moving the anchor from a passive configuration to an active configuration to insert anchoring elements of the anchor

706 detecting an electronic signal at the electrode of the biosensor, the electronic signal being detected in response to an electrochemical reaction between the reactive substance of the biosensor and the analyte to be monitored

DEVICE, SYSTEM AND METHOD FOR MONITORING AN ANALYTE CONCENTRATION IN A FOETUS

CROSS-REFERENCE TO RELATED APPLICATIONS

This application is a National Phase of International Application No. PCT/AU2019/051067, filed Oct. 1, 2019 and titled "A DEVICE, SYSTEM AND METHOD FOR MONITORING AN ANALYTE CONCENTRATION IN A FOETUS" which claims priority to Australian Patent Application No. 2018903727, filed Oct. 2, 2018, and titled "A DEVICE, SYSTEM AND METHOD FOR MONITORING AN ANALYTE CONCENTRATION IN A FOETUS," the entire disclosures of which are herein incorporated by reference in their entirety.

TECHNICAL FIELD

The present invention relates to a device, system and method for monitoring an analyte concentration in a foetus. In particular, the present invention relates to a device, system and method for monitoring a lactate concentration in foetal tissue.

BACKGROUND

During labour and delivery, there is a risk of damage to the foetal brain, neurological system and other end organs as a result of hypoxia, otherwise known as foetal asphyxia. Foetal asphyxia can cause long term, debilitating sequelae for the baby and their family.

Currently, clinicians monitor uterine contractions and foetal heart rate (FHR) using a cardiotocograph (CTG) wherein a change in signal patterns may indicate foetal asphyxia. However, the change in signal patterns are typically only assessed subjectively which has led to a high number of false positives. As a consequence, many caesarean sections are performed based upon fallacious indication of foetal distress as a defensive measure to reduce the risk of intrapartum foetal asphyxia. Due to the large number of false positives, the rate of non-elective caesarean sections has increased. However, caesarean sections come with a number of problems. For example, caesarean sections are associated with increased morbidity for the mother, longer recovery times, and higher rates of post-partum infections (to name a few). Furthermore, caesarean sections are higher in costs than vaginal deliveries.

It would be advantageous if at least an embodiment of the present invention provided a method to monitor a parameter associated with foetal asphyxia continuously and in real-time, or at least provide an alternative to conventional devices and methods.

Any discussion of documents, acts, materials, devices, articles or the like which have been included in the present specification is not to be taken as an admission that any or all of these matters form part of the prior art base or were common general knowledge in the field relevant to the present invention as it existed before the priority date of each claim of this application.

Throughout the specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

Embodiments of the present invention relate to a device for monitoring a concentration of an analyte in a foetus, the device comprising:

a biosensor for electrochemically measuring a concentration of an analyte in the foetus, the biosensor comprising a reactive substance and an electrode, a protrusion configured to be at least partially inserted into foetal tissue, the protrusion comprising at least part of the biosensor, and a device body for supporting the biosensor and the protrusion, the device body being configured to contact a surface area of the foetal tissue;

wherein the device is configured such that when the device body contacts the surface area of the foetal tissue, the device body can be anchored to the foetal tissue to be secured against the contacted surface area of the foetal tissue and the protrusion can be at least partially inserted into the foetal tissue so that the analyte in the foetal tissue electrochemically reacts with the reactive substance of the biosensor and in response to the electrochemical reaction electrode of the biosensor detects an electronic signal, wherein a strength of the electronic signal is indicative of the concentration of the analyte or a rate of change of concentration of the analyte.

Thus, embodiments of the present invention enable the real-time monitoring of a concentration of a selected analyte in the foetus. In this way, foetal oxygen metabolism end products and metabolites of the foetus can be examined in real-time which may provide an indication of the well-being of the foetus during labour and delivery. Furthermore, the process of electrochemically detecting a concentration of the analyte in the foetus may be less invasive for the foetus, as it may not be necessary to take a sample of tissue or blood from the foetus.

The foetal tissue may, for example, be located at a scalp of the foetus. However, it will be appreciated that the foetal tissue may be located at a different body part of the foetus, for example, if the foetus is in breech position.

The protrusion may be in the form of a needle. For example, an outer surface area of the needle may be coated with the reactive substance of the biosensor. The needle may furthermore function as the electrode of the biosensor. Thus, by inserting the needle into the foetal tissue, the reactive substance can electrochemically react with the analyte in the tissue. In this example, the biosensor may be configured to withstand forces when the needle is inserted into the biological tissue. Alternatively, the protrusion may be in the form of a rod or a wire.

In an embodiment, the needle may comprise a hollow space wherein the biosensor is at least partially located within the hollow space. In one particular example, the needle comprises an opening to the hollow space within a side wall or at a tip of the needle to expose the biosensor to an outer surface of the needle such that when the needle is inserted into the tissue, the reactive substance can electrochemically react with the analyte in the foetal tissue at the opening. The opening may, for example, be in the form of a slit or a cut out.

In a further example, the needle may comprise a hollow, tubular space and the needle may be moveable relative to the biosensor that is located within the hollow, tubular space of the needle. Thus, when the needle together with the biosensor has been inserted into the foetal tissue, the needle can be retracted while at least a portion of the biosensor remains within the foetal tissue. In addition, the needle may comprise an opening within a side wall of the needle that forms a track for guiding movement of the needle relative to the biosensor.

The needle may be made of any suitable material, including but not limited to stainless steel, biocompatible material, biological material, synthetic material and biodegradable material. The protrusion may have a length between 0.5 mm and 3 mm, or 1 mm and 2.5 mm or 1.5 mm and 2.5 mm or 1 mm and 2 mm or of approximately 1 mm, 1.5 mm, or 2 mm.

In one embodiment, the protrusion may be configured to form an anchor for anchoring the device body to the foetal tissue. Alternatively, the device may comprise an anchor for anchoring the device body to the foetal tissue, wherein the anchor forms a separate component to the protrusion.

In the following, the term "anchor" may refer to either of the above alternative embodiments.

In an embodiment, the anchor may be in the form of a spiral or hook and the device may be configured such that the device body can be anchored to the foetal tissue by rotating the device body.

In one particular example, the anchor may be moveable from a passive configuration to an active configuration to anchor the device to the foetal tissue. The anchor may be spring-loaded. Specifically, the anchor may be coiled and configured to form a closed loop enclosing a portion of foetal tissue to anchor the device body to the foetal tissue when the anchor is in the active configuration.

The device body may further comprise a flexible material layer covering the surface area for contacting the foetal tissue. The surface area of the device body may be shaped to substantially conform to a shape of the foetal tissue.

In one embodiment, the device body may be substantially flat. This has the particular advantage that the device body that is secured to the foetal scalp has a relatively low profile. Additionally or alternatively, the device body may be substantially dome shaped, wherein the protrusion and/or the anchor are positioned at a substantially flat base of the dome-shaped device body. Alternatively, the device body may have a substantially cylindrical shape, wherein the protrusion and/or the anchor are positioned at a proximal end of the device body.

The device may further comprise a guiding element that is configured such that the device body can be guided through the vaginal canal and the dilated cervix to position the device body against the foetal tissue. The guiding element may be attachable to the device body. For example, the guiding element may comprise a tube with a hollow portion and the device body may be positionable within the hollow portion of the guiding tube. Specifically, the guiding element may comprise a base tube and a sleeve that is movable relative to the base tube, wherein the guiding element may be configured such that a space for holding the device body is formed between the base tube and the sleeve.

The device body may comprise at least one recess for receiving at least a portion of the protrusion and/or the anchor when the anchor is in the passive configuration. In this way, the protrusion and/or the anchor can be at least partially concealed when the device body is guided through the vaginal canal and the at least partially dilated cervix.

The protrusion comprising at least part of the biosensor may protrude from a substantially central point of the substantially flat surface area of the device body.

The anchor may be configured such that when the anchor is inserted into the foetal tissue, the device body is held firmly against the foetal tissue. In this way, the anchor may provide sufficient resistance to withstand forces applied to the device during labour and delivery.

In an embodiment, the device may comprise an actuator for inserting the protrusion into the foetal tissue and/or for anchoring the device body to the foetal tissue. A person skilled in the art will appreciate that the device may comprise multiple actuators to control respective components of the device. This may be particularly applicable if the anchor is a separate component from the protrusion. In one embodiment, the actuator may be configured to move the anchor from the passive configuration into the active configuration. The actuator may be in the form of a push or pull mechanism, a push-pull mechanism, a switch or a torsional mechanism.

In an embodiment, the device may further comprise a component for monitoring a heart rate. The component may comprise a foetal electrode for monitoring a heart rate of the foetus. In addition, the component may comprise a maternal electrode for monitoring a heart rate of the mother. For example, the device may comprise a further protrusion configured to be inserted into the foetal tissue, wherein the further protrusion forms at least part of the foetal electrode for monitoring the heart rate of the foetus. In one particular embodiment, the protrusion and the further protrusion may extend substantially parallel to each other, such as in a substantially straight direction or coiled. In one embodiment, the further protrusion may be in the form of a needle configured to be at least partially inserted into the tissue area of the foetus.

In an alternative embodiment, the protrusion comprising at least part of the biosensor may also comprise the foetal electrode for monitoring the heart rate of the foetus. In this example, the device is configured such that the electrode of the biosensor and the foetal electrode are electrically isolated from each other. In another example, the anchor may comprise at least part of the foetal electrode for monitoring a heart rate of the foetus. For example, the further electrode may be located at a tip of an anchoring element, such as a curved or straight leg.

In an embodiment, the device is configured such that the biosensor can detect the concentration of the analyte in foetal tissue such as the extracellular matrix. Additionally or alternatively, the device may be configured such that the biosensor can detect the concentration of the analyte in foetal blood.

In one specific embodiment, the analyte to be monitored may be lactate. The concentration of lactate in the foetus may be monitored in foetal tissue and/or foetal blood. However, other analytes are envisaged, including but not limited to glucose, cortisol, pyruvate, activin A, bicarbonate, hydrogen ions, non-protein bound iron, hypoxanthine and other suitable analytes that may be indicative of a well-being of the foetus.

In a specific embodiment, the device comprises a plurality of biosensors to monitor the concentration of a plurality of analytes.

In an embodiment, the reactive substance of the biosensor comprises an immobilised enzyme. The biosensor may be coated with the immobilised enzyme. If the device is configured to monitor a concentration of lactate of the foetus, the immobilised enzyme may, for example, be lactate oxidase or lactate dehydrogenase. However, other suitable enzymes are envisaged. A person skilled in the art will appreciate that the substance may be selected depending on the analyte to be monitored for the electrochemical reaction to occur.

The device may further comprise an analysis component for analysing the detected electronic signal(s). The analysis component may be part of a computing device comprising a processor. The processor may be configured to determine an absolute concentration of the analyte in the foetus. In one embodiment, the analysis component is configured to determine whether the concentration of the analyte exceeds or falls below a predetermined threshold.

The analysis component may be housed in an external housing and in electronic communication with the biosensor and/or the further electrode for detecting the heart rate of the foetus. For example, the analysis component may be connected to the biosensor and/or the further electrode through a wire. The wire may extend through the guiding tube.

The external housing may be attachable to a body part of the mother. For example, the external housing may comprise a strap for attaching the analysis component to a leg of the mother. However, other configurations are envisaged. For example, the device may comprise a wireless transmitter for transmitting the detected electronic signal to a computing device, such as a mobile computing device.

The device may be configured to monitor the concentration of the analyte in real-time. For example, the device may be configured to monitor the concentration of the analyte continuously, periodically or upon request.

In accordance with embodiments of the present invention, there is provided a system for monitoring a concentration of an analyte in a foetus, the system comprising:

a biosensor for electrochemically measuring a concentration of an analyte in the foetus, the biosensor comprising a reactive substance and an electrode, a protrusion configured to be at least partially inserted into foetal tissue, the protrusion comprising at least part of the biosensor, a device body for supporting the biosensor and the protrusion, the device body being configured to contact a surface area of the foetal tissue, and an analysis component in electronic communication with the electrode of the biosensor, the analysis component being configured to determine information indicative of the concentration of the analyte using the detected electronic signal of the biosensor, wherein the system is configured such that when the protrusion is at least partially inserted into the tissue, the device body can be anchored to the foetal tissue to be secured against the contacted surface area of the foetal tissue, and the analyte electrochemically reacts with the reactive substance of the biosensor such that in response to the electrochemical reaction the electrode of the biosensor detects an electronic signal, a strength of the electronic signal being indicative of the concentration of the analyte.

In one embodiment, the analysis component is configured to determine a trend of a baseline concentration of the analyte. The analysis component may be configured to determine whether the concentration of the analyte exceeds or falls below a predetermined threshold.

In one embodiment, the analysis component may be configured to determine an absolute concentration of the analyte in the foetus.

The system may comprise a computing device comprising the analysis component, for example, in the form of a processor. The computing device may further comprise a display for displaying information indicative of the concentration of the analyte in the foetus. The information may be displayed in real-time.

The system may comprise an external housing for housing the analysis component. The external housing may comprise an attachment for attaching the external housing to a body part of the mother. For example, the external housing may comprise a strap for attaching the external housing to a leg or belly of the mother.

The analysis component may also be in electronic communication with the foetal electrode and/or the maternal electrode. The analysis component may be connected to the biosensor, the foetal electrode and/or the maternal electrode through a wire. The wire may extend through a guiding tube of the device. Alternatively, the device may comprise a wireless transmitter for transmitting the detected electronic signal to a computing device, such as a mobile computing device.

In accordance with embodiments of the present invention, there is provided a method of monitoring a concentration of an analyte in a foetus, the method comprising:

providing a device for monitoring a concentration of an analyte in a foetus, the device being configured to be anchored to foetal tissue and comprising a protrusion for being at least partially inserted into foetal tissue;

inserting the protrusion at least partially into foetal tissue, the protrusion comprising at least part of a biosensor, the biosensor comprising a reactive substance and an electrode;

when the protrusion has been at least partially inserted into the foetal tissue, anchoring the device to the foetal tissue; and detecting an electronic signal at the electrode of the biosensor, the electronic signal being in response to an electrochemical reaction between the reactive substance of the biosensor and the analyte to be monitored;

wherein the method is conducted such that the detected electronic signal is indicative of the concentration of the analyte in the foetus.

In one embodiment, the protrusion is at least partially inserted into the foetal tissue such that the reactive substance can react with the analyte in the foetal tissue and/or foetal blood.

The method may comprise a step of guiding the device through the vaginal canal and dilated cervix. Specifically, the method may comprise a step of providing a guiding element comprising a base tube and a sleeve and positioning the device in a space formed between the base tube and the sleeve. When the protrusion has been inserted into the foetal tissue and the device body has been anchored to the foetal tissue, the method may comprise a step of removing the guiding element from the device.

The invention will be more fully understood from the following description of specific embodiments of the invention. The description is provided with reference to the accompanying drawings.

BRIEF DESCRIPTION OF DRAWINGS

FIG. 14 shows a flow chart illustrating a method of monitoring a concentration of an analyte in a foetus in accordance with an embodiment of the present invention.

DESCRIPTION OF EMBODIMENTS

Figure 1:
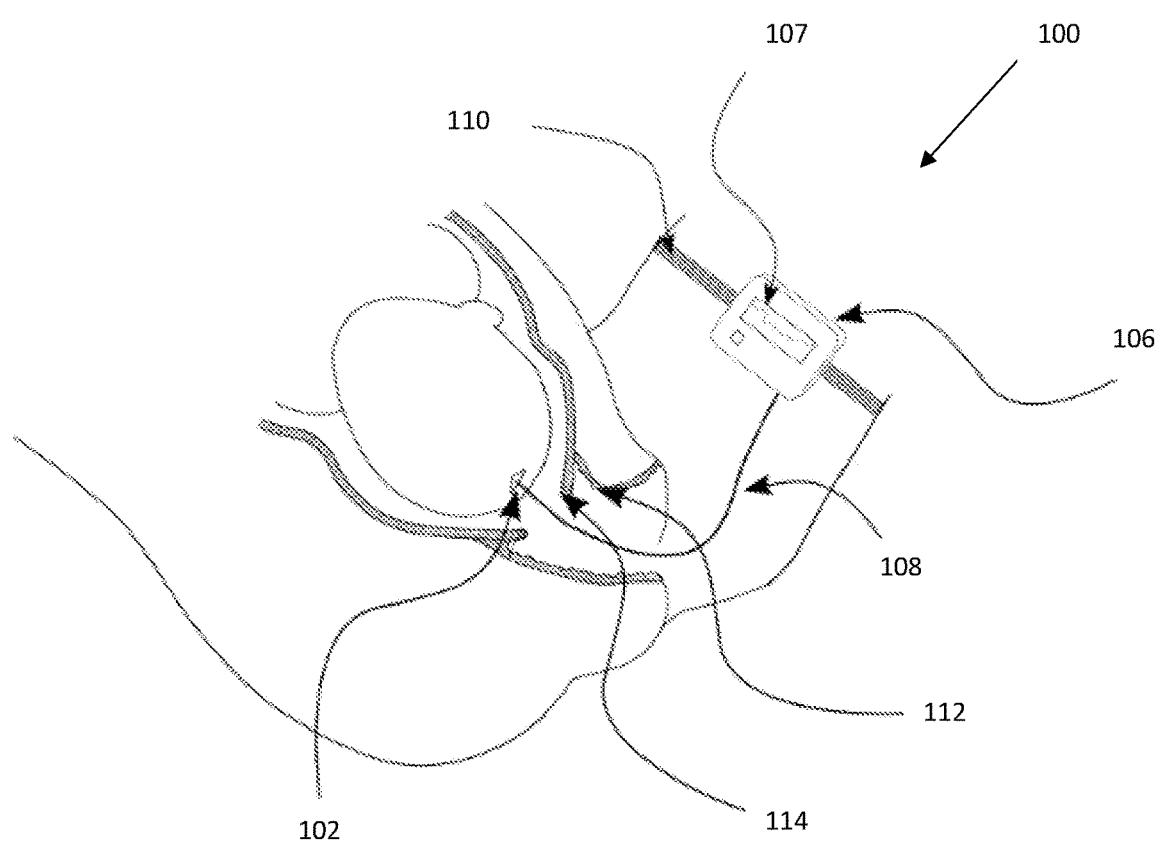
FIG. 1 is a schematic representation of a system for monitoring a concentration of an analyte in a foetus in accordance with an embodiment of the present invention.

Embodiments of the present invention generally relate to a device, a system and a method for monitoring a concentration of an analyte in a foetus. The device according to embodiments of the present invention comprises a biosensor for electrochemically measuring a concentration of an analyte in the foetus, such as a concentration of lactate in foetal tissue. The biosensor comprises a reactive substance that is selected to be reactive with the analyte to be monitored and an electrode for detecting an electronic signal. The device further comprises a protrusion configured to be at least partially inserted into foetal tissue, wherein the protrusion comprises at least part of the biosensor. For example, the protrusion may be in the form of a needle that is coated with the reactive substance of the biosensor. In this way, the reactive substance of the biosensor can be positioned within the foetal tissue. Alternatively, the protrusion may be in the form of a needle comprising a hollow space wherein the biosensor is provided within the hollow space. In this example, the outer portion of the needle may be retractable thereby positioning only the biosensor within the foetal tissue, or the needle may have an opening thereby exposing the biosensor to an outer surface of the needle.

The device further comprises a device body for supporting the biosensor and the protrusion. The device body typically has a relatively low profile and may be attachable to a guiding element to facilitate positioning of the device body against foetal tissue via the vaginal canal and the sufficiently dilated cervix of the mother.

The device is configured such that the device body can be anchored to the foetal tissue and the protrusion is at least partially inserted into the foetal tissue. In this regard, the protrusion may be configured as an anchor, or alternatively the device may comprise an anchor that forms a separate component from the protrusion. In the following, the term "anchor" may refer to the protrusion configured as an anchor or the anchor as separate component. The anchor may comprise a coiled anchoring element, for example, in the form of a hook or a spiral that can be anchored within the foetal tissue. Additionally or alternatively, the anchor may be movable from a passive configuration to an active configuration to anchor the device body in the foetal tissue. The anchor may also be movable from the active configuration to the passive configuration to remove the device body from the foetal tissue once the monitoring of the analyte has been completed.

The device is configured such that when the protrusion is at least partially inserted into the tissue, the reactive substance of the biosensor electrochemically reacts with the analyte such that in response to the electrochemical reaction the electrode of the biosensor detects an electronic signal. A strength of the electronic signal is indicative of the concentration of the analyte or a rate of change in concentration of the analyte. In some embodiments, the device further comprises a component for monitoring a heart rate, such as a foetal electrode for monitoring a foetal heart rate and a maternal electrode for monitoring a maternal heart rate.

Embodiments of the present invention have significant advantages which will become more apparent in light of the detailed description of exemplary embodiments of the present invention.

As mentioned in the background section, false positive indications of foetal distress as a result of conventional methods of monitoring the well-being of a foetus through heart rate monitoring may result in an increase in caesarean sections to reduce the time of the delivery. One method to monitor the well-being of a foetus relates to collecting a sample of foetal blood to determine foetal blood lactate levels. Lactate is a metabolite produced during glucose metabolism in the presence of asphyxia. The sample of foetal blood is typically collected from the foetal scalp or umbilical arteries at the delivery. The sample is then analysed for the concentration of lactate which is produced when the foetus does not have enough oxygen and undergoes anaerobic respiration. However, this method has a number of disadvantages. For example, the method is relatively invasive for the foetus and the mother. Due to its complexity it is difficult to perform which results in a median time of approximately 20 minutes. However, the method often takes longer and can be painful, uncomfortable and undignified for women and their doctor. Even more so, complications such as hematoma, bleeding from the scalp, and death can occur as a result of this complex procedure.

Embodiments of the present invention aim to reduce the complexity and invasiveness. Furthermore, at least an embodiment of the present invention enables the monitoring of the selected analyte, such as lactate, continuously and in real-time. As such, a doctor or midwife can act immediately once the lactate levels exceed a predetermined threshold.

Furthermore, by using an electrochemical reaction between the biosensor and the analyte to be monitored, it may not be necessary to collect a sample of blood or tissue. This is different to the conventional method and other methods, such as micro-dialysis.

Referring now to the drawings, FIG. 1 shows a system 100 for monitoring a concentration of an analyte in a foetus. The system 100 comprises a device 102 to be secured to foetal tissue, in this example to a foetal scalp 104. A person skilled in the art will appreciate that the device 102 may be attachable to a different body part of the foetus, for example, if the foetus is in breech position. The device 102 is in electronic communication with an analysis component 106 via a wire 108. The analysis component 106 is typically a computing device comprising a processor that is, in this example, housed in an external housing 106 with a display 107 to display information indicative of the concentration of the lactate. The external housing 106 has a strap 110 for attaching the analysis component 106 to the mother. In this example, the analysis component 106 is attached to a leg of the mother. However, the analysis component 106 may alternatively be attached to the belly of the mother or any other suitable body part. Attaching the analysis component 106 to the leg of the mother has the advantage that the length of the wire 108 can be kept relatively short and allows the mother to move around freely, walk and shower.

The device 102 comprises at least a biosensor for sensing a concentration of the analyte, in this particular example, a concentration of lactate. The concentration of lactate is typically sensed in the foetal tissue, but may also be sensed in foetal blood. In the following examples, the device 102 also comprises a foetal electrode for detecting a heart rate of the foetus and a maternal electrode for detecting a heart rate of the mother as will be described in further detail below. However, a person skilled in the art will appreciate that other methods may be used to detect the heart rate of the foetus and/or the mother.

The device 102 is positioned at the foetal scalp via the vaginal canal 112 and a sufficiently dilated cervix 114. This may be done by attaching the device 102 to a guiding element such as a guiding tube. If the device 102 has a width between 0.3 and 4 cm, the device 102 can be positioned at the foetal scalp at an early phase of maternal dilation ranging from 2 to 4 cm.

Figure 2:
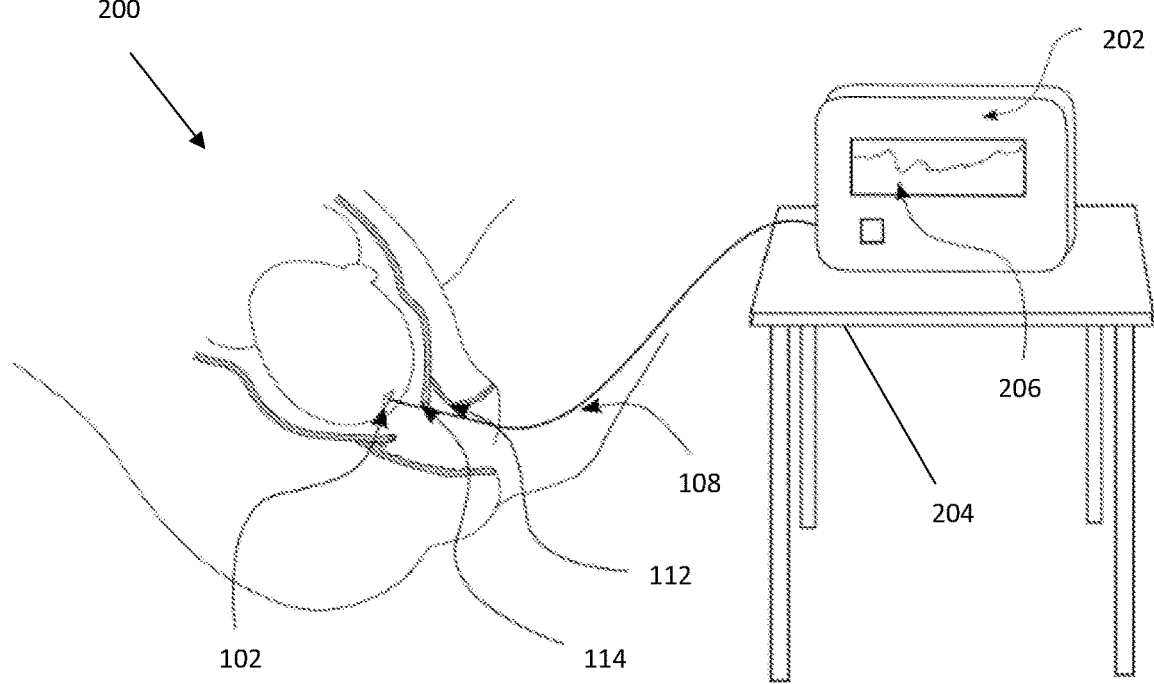
FIG. 2 is a schematic representation of a system for monitoring a concentration of an analyte in a foetus in accordance with a further embodiment of the present invention.

An alternative exemplary system 200 in accordance with an embodiment of the present invention is illustrated in FIG. 2. In this example, like numerals refer to like components of the system 200. The system 200 also comprises the device 102 attachable to the foetal scalp 104. In this example, the device 102 is in electronic communication with an external monitoring device 202 that may be positioned on a bedside table 204. In this example, the external monitoring device 202 is connected to the device 102 via the wire 108. However, a person skilled in the art will appreciate that the device 102 may be connected to the external monitoring device 202 wirelessly. In such case, the device 102 may comprise a transmitter for wirelessly transmitting an electronic signal to a computing device. The computing device may be the external monitoring device 202, but may alternatively be a smartphone, tablet, laptop or personal computer.

The external monitoring device 202 comprises a display 206 for displaying information indicative of the concentration of the analyte. The information may be in any suitable form. For example, the absolute concentration of the analyte may be displayed using numbers or a graph. Additionally or alternatively, a trend from a baseline concentration may be displayed. In this way, a doctor or midwife may be able to monitor the concentration of the analyte continuously and in real-time. Thus, if the information indicative of the concentration of lactate exceeds or falls below a predetermined threshold, the doctor or midwife are able to intervene immediately.

Figure 3:
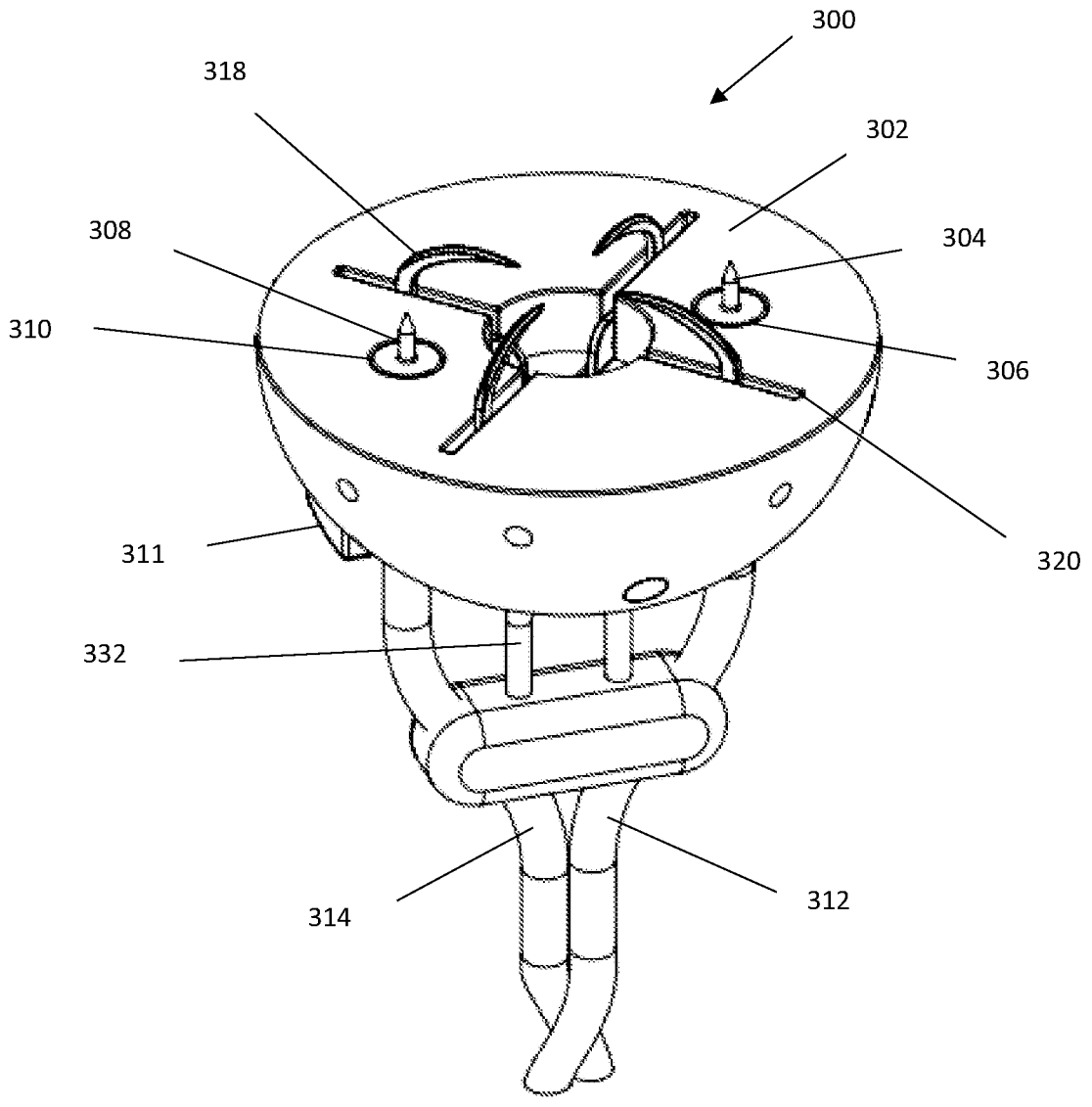
FIGS. 3 to 5 show different views of a device for monitoring a concentration of an analyte in a foetus in accordance with an embodiment of the present invention.
Figure 4:
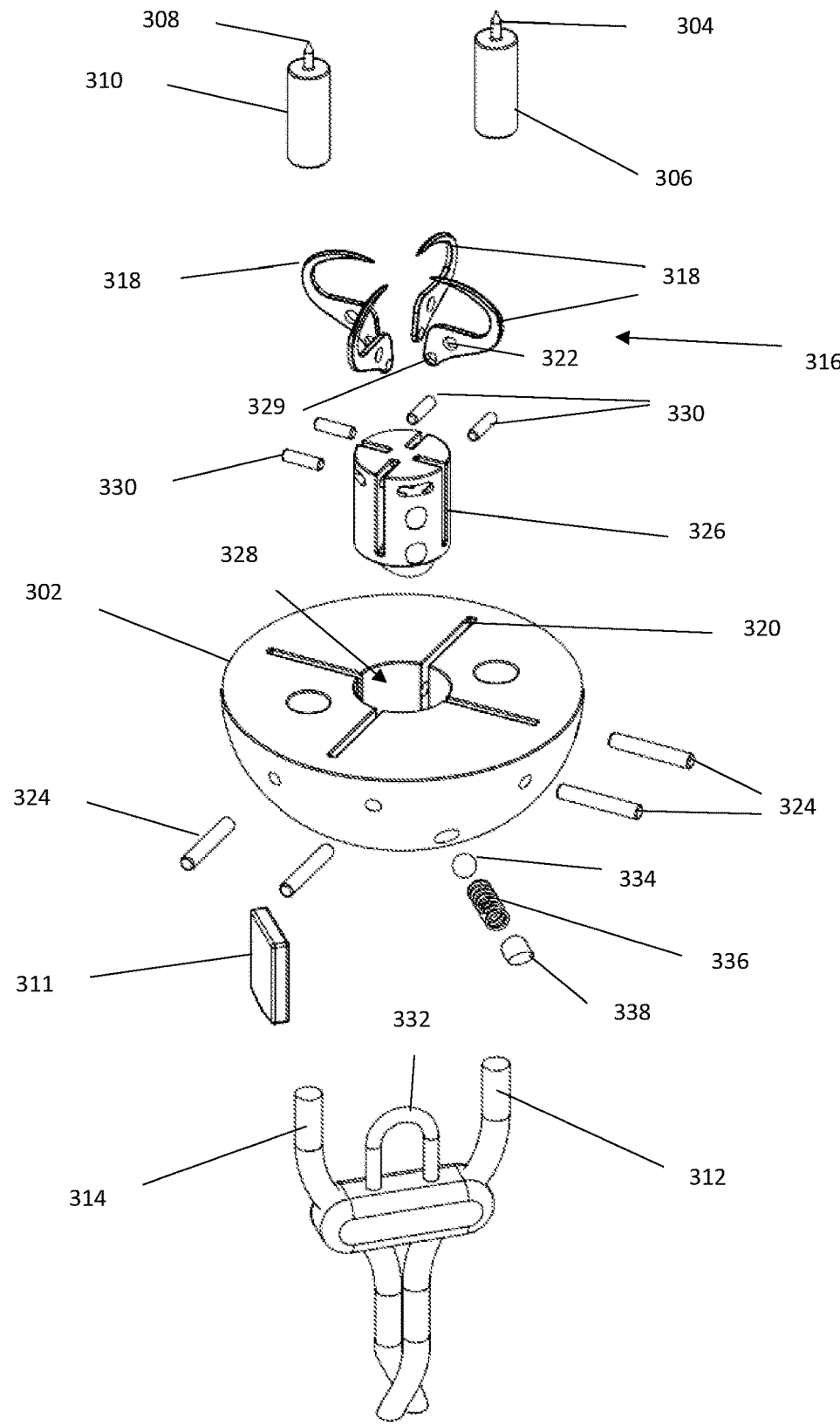
Figure 5:
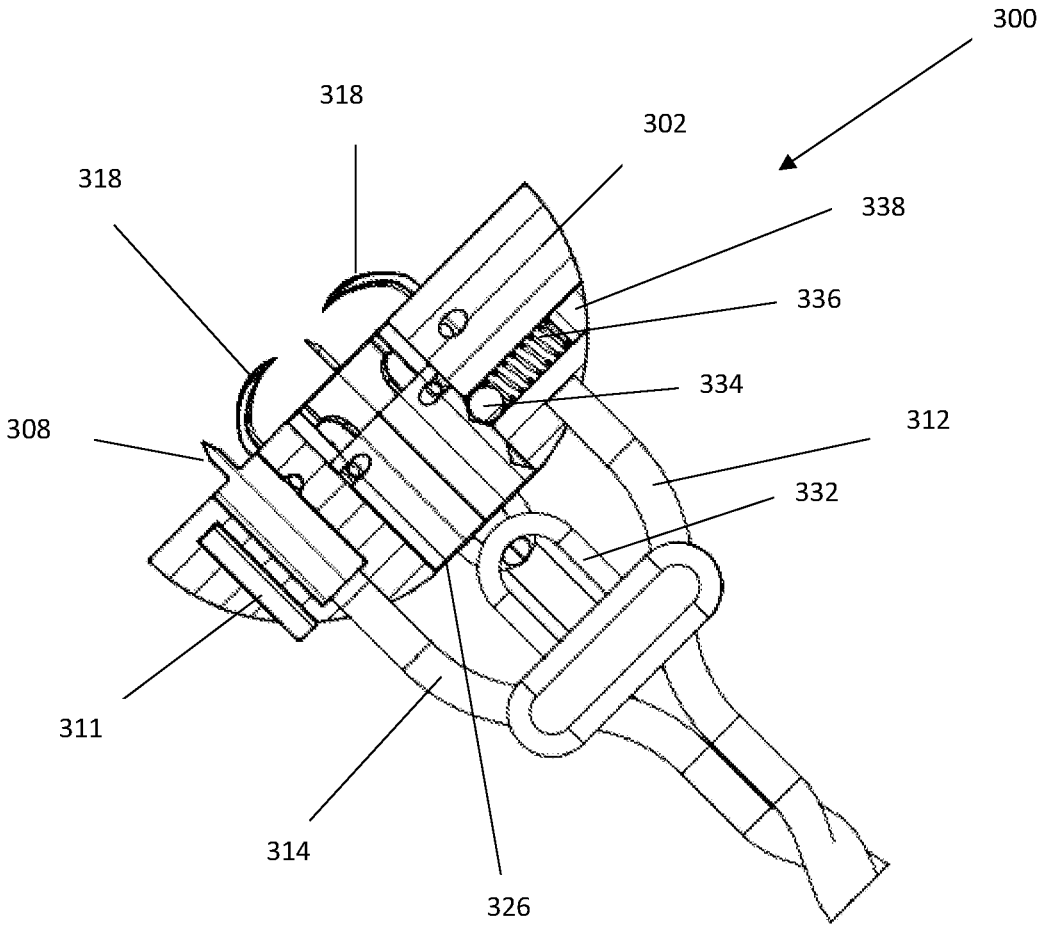

Referring now to FIGS. 3 to 5, there is shown a device 300 for monitoring a concentration of an analyte in accordance with a first embodiment of the present invention. In this example, the device 300 is configured to monitor a concentration of lactate. The device 300 may for example be the device 102 as part of the system 100 or system 200 shown in FIGS. 1 and 2.

The device 300 comprises a device body 302 that can be positioned against foetal tissue, such as a surface area of a foetal scalp. In this particular example, the device body 302 is substantially dome shaped having a substantially flat surface area to face the foetal tissue and a rounded portion configured to face away from the foetal tissue. Thus, the device 300 has a relatively low profile which is advantageous when the device 300 is in use. Exemplary heights of the device body may be in the range of approximately 2 to 20 mm, or 2 to 15 mm, or 5 to 15 mm, or 5 to 10 mm, or approximately 5 mm, 6 mm, 7 mm, 8 mm, 9 mm or 10 mm. When the device 300 is secured to the foetal tissue as will be described below, the substantially flat surface area of the device body 302 may be firmly pressed against the surface area of the foetal tissue to withstand forces applied to the device 102 during labour. The device body may further comprise a flexible material layer (not shown) covering the substantially flat surface area for contacting the foetal tissue. Additionally or alternatively, the surface area may be shaped to substantially conform to a shape of the foetal scalp.

Figure 7:
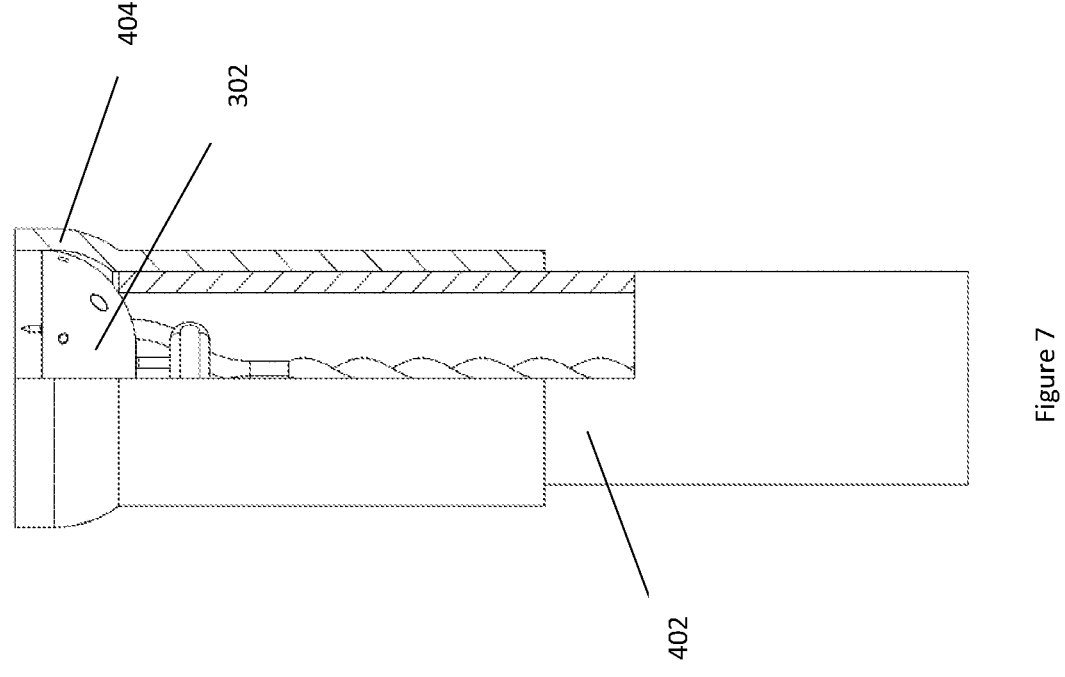
FIGS. 6 and 7 shown different views of a device positioned in a guiding tube in accordance with an embodiment of the present invention.
Figure 6:
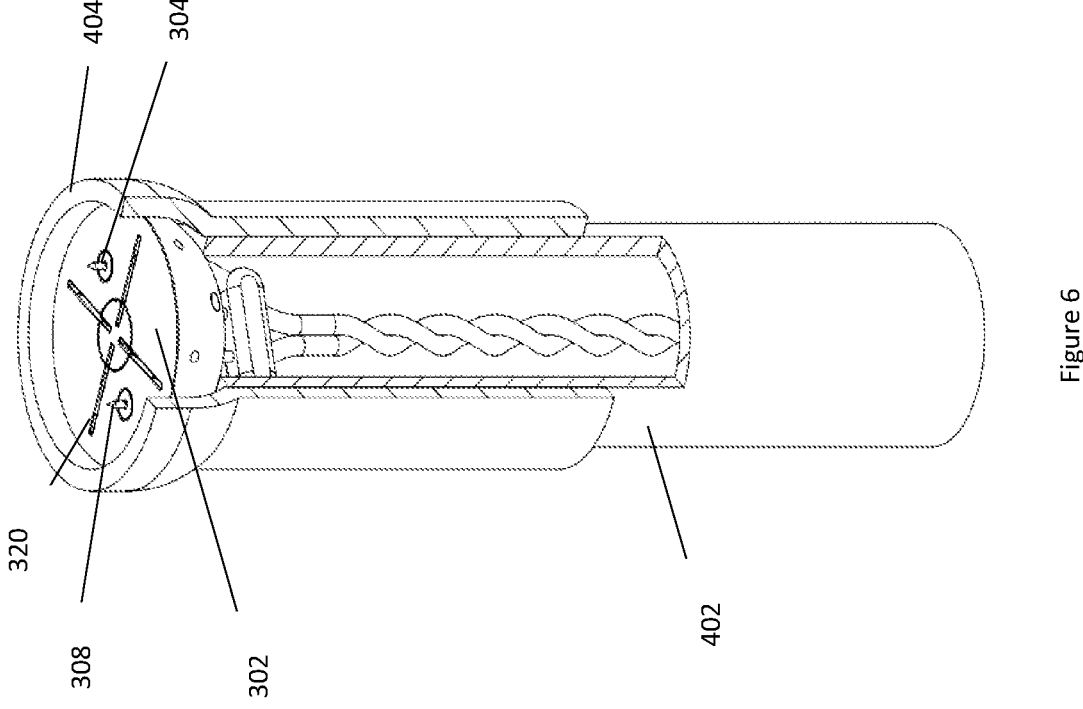

A person skilled in the art will appreciate that the device body may have any suitable shape. For example, the device body may have a substantially cylindrical shape, wherein the protrusion and the anchor are positioned at a proximal end of the device body, as for example shown in the embodiment in FIGS. 11 and 12. In an alternative embodiment, the device body may be substantially flat, such as in the embodiment shown in FIGS. 9 and 10. In a further example, the device body 302 may be substantially flat and attachable to a guiding tube as shown in FIGS. 6 to 8.

Referring back to device 300, the device body 302 supports a first protrusion 304 that can be at least partially inserted into foetal tissue, such as the foetal scalp 104. In this example, the first protrusion 304 is in the form of a relatively short first needle 304 having a length of approximately 2 mm. The needle 304 is configured to be fully inserted into the foetal scalp. In this example, the needle 304 is made of steel. However, other suitable materials are envisaged, including but not limited to biocompatible material, biological material, synthetic material and biodegradable material. The needle 304 may have any suitable length, including but not limited to between 0.5 mm and 3 mm, or 1 mm and 2.5 mm or 1.5 mm and 2.5 mm or 1 mm and 2 mm or of approximately 1 mm, 1.5 mm, or 2 mm.

Figure 13:
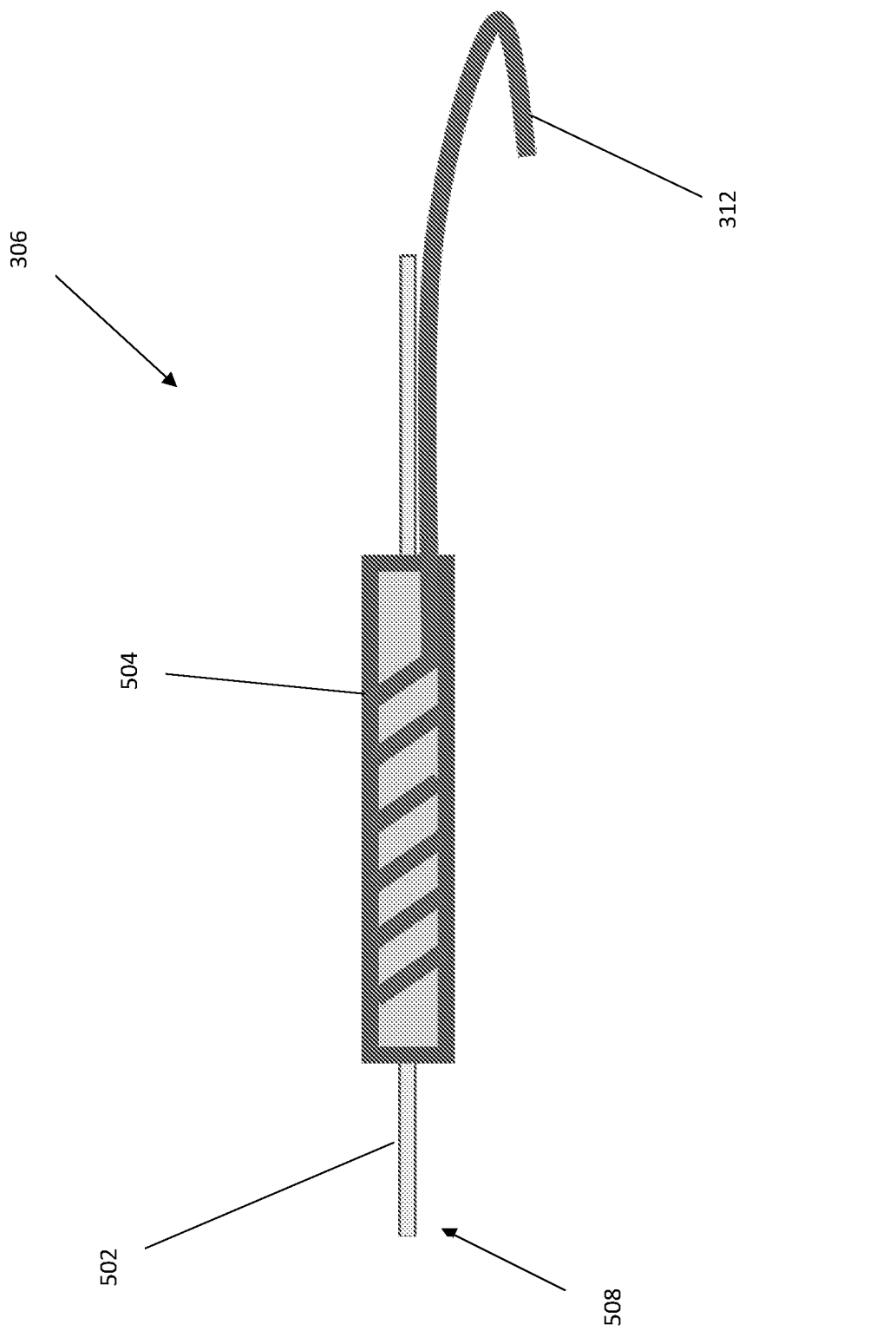
FIG. 13 shows a schematic representation of a biosensor of the exemplary devices of FIGS. 3 to 12.

The first needle 304 is part of a biosensor 306 that is configured to electrochemically measure the concentration of the lactate in the foetal tissue. In this regard, the biosensor 306 comprises a reactive substance and an electrode. A more detailed representation of the biosensor 306 is illustrated in FIG. 13. An electrochemical biosensor typically comprises two elements, a biological element to react with the analyte to be monitored and a transducer element. The interaction between the biological element and the analyte may result in an electrical, optical or thermal signal which can be detected and transformed into a measurable electrical parameter by the transducer element. In this example, the biosensor 306 utilises a three-electrode system comprising a working electrode 502, a reference electrode 504 and a counter current electrode 506. The working electrode 502 has a first end 508 that forms the first needle 304 which is coated in the reactive substance (not shown), in this case an immobilised enzyme, such as lactate oxidase or lactate dehydrogenase. The biosensor 306 is configured to measures a current between the working electrode 502 and the counter current electrode 506 and utilises the principle that the measured current is proportional to a concentration of the lactate in the foetal tissue. The reference electrode 504 may be a Ag/AgCl or saturated calomel electrode which provides a stable and reproducible potential to which the working electrode potential is compared.

When the first end 508 coated with the immobilised enzyme is inserted into the foetal tissue, the immobilised enzyme reacts with the lactate concentrations present in the extra-cellular matrix and blood of the skin and dense connective tissue of the foetal scalp. The enzymatic reaction leads to the formation of peroxide ions, which are electro-chemically detected as chemical reduction events at the working electrode 502 of the biosensor 306. This results in transmission of an electronic signal that is transmitted to an analysis component, such as analysis component 106, via the wire 312. The electronic signal may undergo signal transformation to make available information indicative of the concentration of the lactate in the foetus.

The concentration of the lactate correlates with the strength of the electronic signal. Using this correlation, it may be possible to determine an absolute value of the lactate concentration in the foetal tissue. However, it may be sufficient to determine a trend relative to a baseline concen-tration and/or whether an electronic signal exceeds or falls below a predetermined threshold based on historical data. In order to determine an absolute value of the concentration of lactate in the foetus, a calibration method may need to be conducted. In this regard, a blood sample of the foetus may be taken and examined to determine a reference concentra-tion. Having regard to exemplary values of the absolute concentration of lactate in foetal tissue, a normal range may be considered amounting to less than 4.1 mmol/L, whereas a pre-acidotc range may be defined at a lactate concentration between 4.2 and 4.8 mmol/L and an acidotic range may be above 4.8 mmol/L.

Referring back to FIGS. 3 to 5, the device 300 comprises a second protrusion 308 in the form of a second needle 308. The second needle 308 is part of a foetal electrode 310 for detecting a heart rate of the foetus. Whilst the foetal elec-trode 310 in this example comprises a needle, a person skilled in the art will appreciated that other implementations are envisaged. For example, the foetal electrode may be in the form of a plate configured to contact foetal tissue to detect the foetal heart rate. In addition to the foetal electrode 310 the device 300 also comprises a maternal electrode 311 for detecting a heart rate of the mother. The maternal electrode 311 is configured to contact tissue of the mother, such as the uterus, to monitor the heart rate.

In this particular example, the electrodes of the biosensor 306 and the foetal heart rate monitor 310, 311 are imple-mented having separate needle components. However, a person skilled in the art will appreciate that the electrodes may be combined into one component as long as the electrodes are electronically isolated from each other. Fur-thermore, the foetal electrode 310 and/or the biosensor 306 may be incorporated in other components of the device 300, such as in anchoring elements or surface elements of the device body 302, as will be described in the embodiment shown in FIGS. 9 and 10.

Furthermore, a person skilled in the art will appreciate that the device 300 may comprise additional sensors that may be incorporated in additional or existing components, such as the protrusions. For example, the device may comprise multiple biosensors to monitor multiple analytes, including but not limited to glucose, cortisol, pyruvate, activin A, bicarbonate, hydrogen ions, non-protein bound iron, hypoxanthine and other suitable analytes that may be indicative of a well-being of the foetus.

The foetal electrode 310, the maternal electrode 311 and the electrode of the biosensor 306 are electronically con-nected to an external analysis component via wires 310, 312. In this example, the wires 310, 312 have a further function of facilitating activation of anchoring elements of the device 300 as described below.

The device 300 comprises an anchor 316 comprising anchoring elements 318 for holding the device body 302 in place when the first and second needles 304, 308 have been inserted into the foetal tissue. In this example, the anchor 316 comprises four anchoring elements 318 in the form of hooks 318. The anchor 316 can be moved from a passive configuration to an active configuration and vice versa. In this regard, the device body 302 comprises a plurality of recesses 320 that are sized and shaped to receive the respective hooks 318 when the anchor 316 is in the passive configuration. In this example, the recesses 320 are in the form of slits that are arranged in a cross formation. However, other configurations are envisaged.

When the anchor 316 is in the passive configuration, the four hooks 318 are positioned within the respective recesses 320. In this way, it can be avoided that the hooks 318 interact with surrounding tissue when the device 300 is guided through the vaginal canal and the sufficiently dilated cervix. Once the device body 302 is positioned against the foetal tissue, the anchor 316 is moved into the active configuration and the hooks 318 pivot towards each other about a pivot axis 322. The device body 302 comprises respective pins 324 about which the hooks 318 pivot. Thus, end portions of the hooks 318 move outside of the recesses 320 and enter the foetal tissue. In this way, the device body 302 can be anchored to the foetal tissue. Once the hooks 318 are inserted into the foetal tissue, the device body 302 is held firmly against the foetal tissue. In this way, the anchor 316 can provide sufficient resistance to withstand forces applied to the device 300 during labour and delivery of the foetus.

A person skilled in the art will appreciate that the anchor may have any suitable anchoring elements configured to secure the device body 302 to the foetal tissue. For example, the anchor may comprise any suitable number of legs that can be inserted into the foetal tissue. The legs may be curved to form hooks, or substantially straight. The legs may comprise a barbed end. In one alternative example (not shown), the anchoring elements may be in the form of a plurality of substantially straight legs that enter the foetal tissue at different angles to secure the device body 302 to the foetal tissue. Specifically, the plurality of substantially straight legs may fan out such that a distance between adjacent legs increases with increasing depth in the foetal tissue.

To move the anchor 316 from the passive configuration into the active configuration, the device 300 comprises an activator. In this particular example, the activator is in the form of a push-pull mechanism and comprises cylinder 326 that is positioned within a central channel 328 of the device body 302. The cylinder 326 has two opposite ends, wherein one end is connected to the hooks 318 via a driving axis 329. For this, the cylinder 326 comprises respective driving pins 330. The other, distal end of the cylinder 326 is connected to the first and second wires 312, 314, for example, via a hook and loop connection 332.

The device 300 is configured such that the cylinder 326 can move laterally within the central channel 328 of the device body 302 to pivot the hooks 318 about the respective pivot axes 326. In this way, the anchor 316 can be moved from the passive configuration into the active configuration and vice versa. Thus, the anchor 316 can be moved from the passive configuration to the active configuration by pulling on the wires 312, 314. By pushing the wires 312, 314 towards the device body 302, the anchor 316 returns from the active configuration to the passive configuration and the hooks 318 are removed from the foetal tissue.

In this particular example, the device 300 further com-prises a locking element for locking the anchor 316 in the passive configuration or the active configuration. The lock-ing element comprises a ball bearing 334 and a spring 336.

The cylinder 326 comprises a locking stops in the form of recesses that are located at a side portion of the cylinder 326. This is particularly shown in the side view of the device 300 in FIG. 5. The ball bearing 334 and the spring 336 are held in place by virtue of a plug 338 so that the spring 336 pushes the ball bearing 334 against the side portion of the cylinder 326.

Referring now to FIGS. 6 and 7, there is shown the device 300 attached to a guiding tube 400. The guiding tube 400 may form part of the device 300. In this particular example, the guiding tube 400 has an overall substantially cylindrical shape and is configured to guide the device body 302 through the vaginal canal and the sufficiently dilated cervix to position the device body 302 against the foetal tissue. A diameter of the guiding tube 400 may be similar to a width of the device body 302, i.e. in a range of approximately 2 and 4 cm, or approximately 2 cm, 3 cm or 4 cm. A length of the guiding tube 400 may be in a range of approximately 5 and 35 cm, 10 and 30 cm, 15 and 25 cm, or 15 to 20 cm, or of approximately 10 cm, 15 cm, 20 cm or 25 cm.

Figures 8A, 8B, 8C, 8D, 8E:
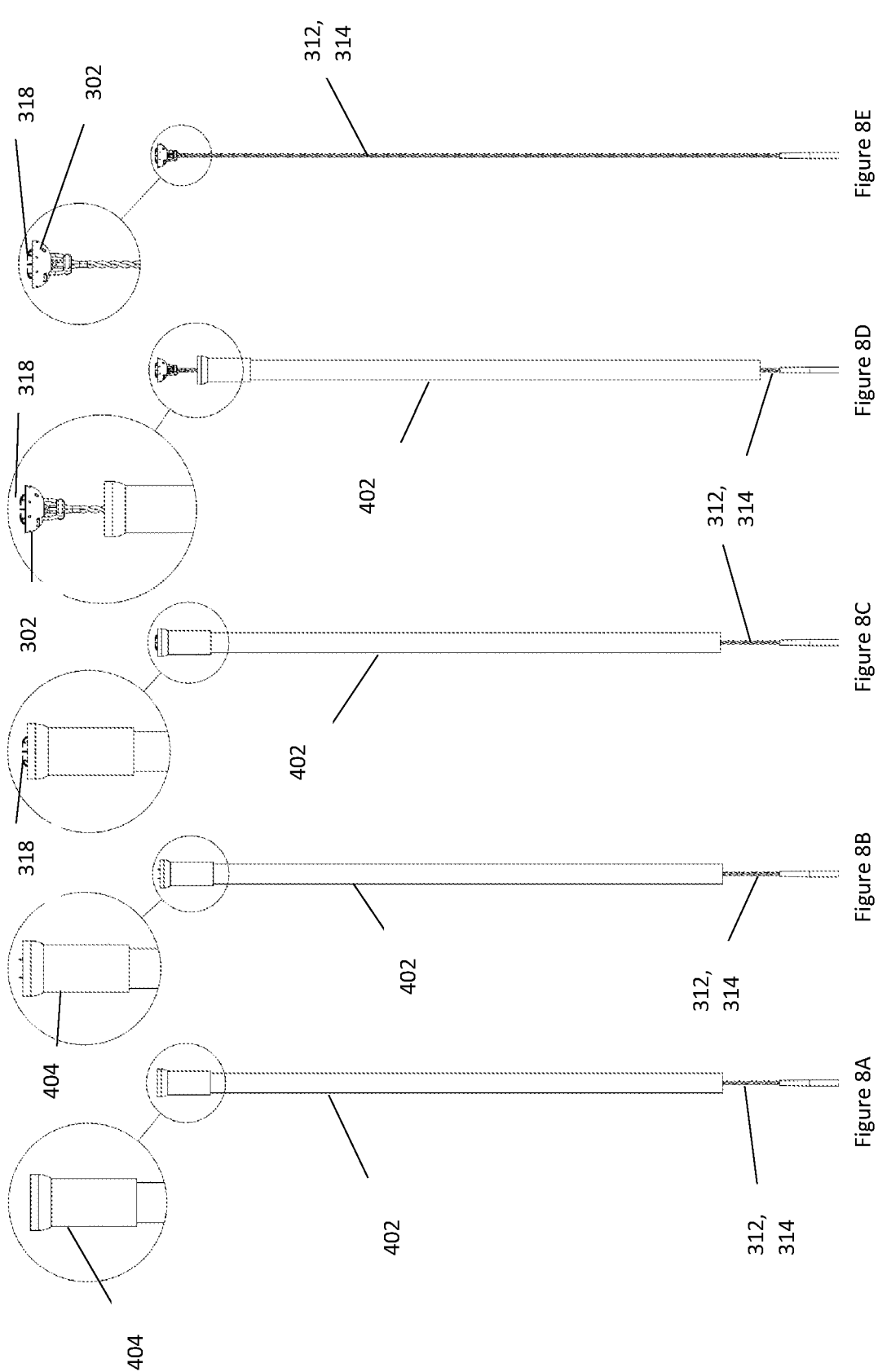
FIGS. 8A to 8E show different configurations of the device and the guiding tube of FIGS. 6 and 7 in accordance with an embodiment of the present invention.

In this example, the guiding tube 400 comprises a base tube 402 having a hollow channel through which the wires 312, 314 extend. The guiding tube 400 further comprises a hollow sleeve 404 that covers an end portion of the base tube 402. The guiding tube 400 is configured such that a space is formed between the base tube 402 and the sleeve 404 to hold the device body 302. In order to position the device body 302 against the foetal tissue, the device body 302 is initially positioned in the formed space between the base tube 402 and the sleeve 404. This particular configuration is shown in FIG. 8A. As shown in the drawing, in this initial configuration the hooks 318 are located in the recesses 320 of the device body 302 so that the hooks 318 cannot engage with surrounding tissue when the guiding tube 400 is moved through the vaginal canal and the cervix.

Once the device body 302 is positioned against the foetal tissue, for example, by pressing the guiding tube 400 against the tissue, a user, such as a doctor or midwife, can pull on the wires 312, 314 to release the hooks 318 and anchor the device body 302 in the foetal tissue. Exemplary configurations of the device 300 and the guiding 400 during this process are shown in FIGS. 8B and 8C. Once the device body 302 is anchored in the foetal tissue, the guiding tube 400 can be removed. Specifically, a doctor or midwife may pull the base tube 402 together with the sleeve 404 to remove the guiding tube 400. By removing the guiding tube 400, comfort for the mother can be significantly improved and may allow for the mother to freely move around.

Figure 9:
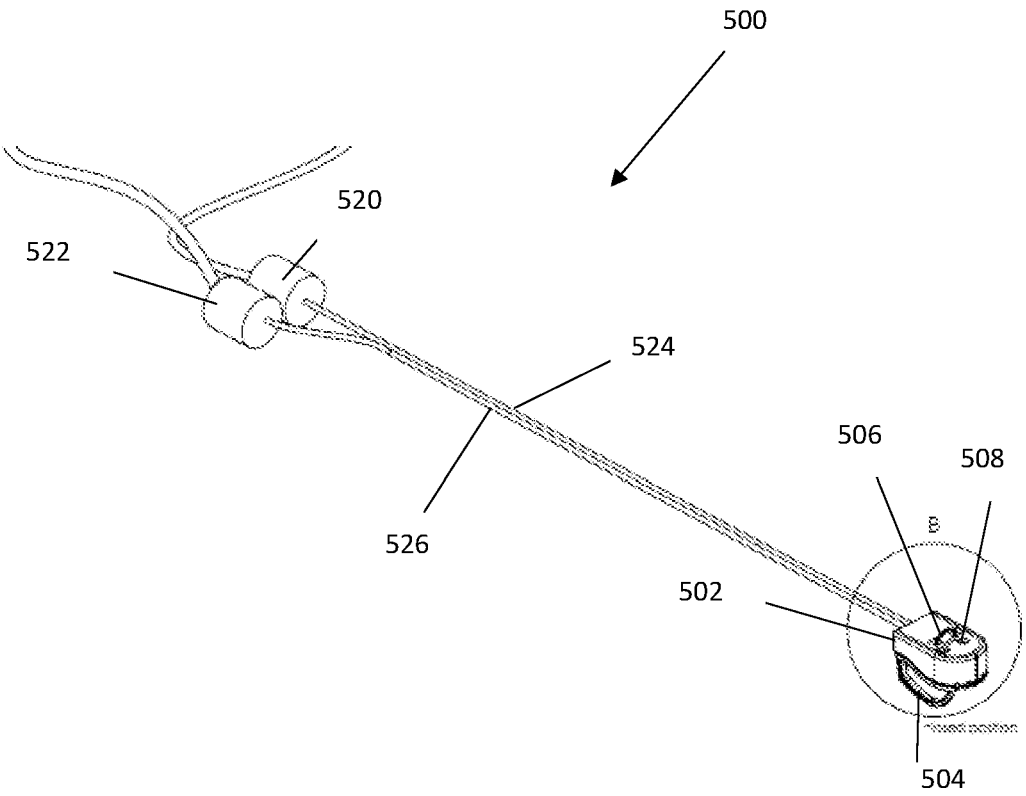
FIG. 9 shows a schematic representation of a device for monitoring a concentration of an analyte in a foetus in accordance with a further embodiment of the present invention.

Referring now to FIGS. 9 and 10, there is shown a device 500 for monitoring a concentration of an analyte in accordance with a further embodiment of the present invention. Similar to device 300, the device 500 in this example is configured to monitor a concentration of lactate in a foetus and may be the device 102 as part of the system 100 or system 200 shown in FIGS. 1 and 2.

The device 500 comprises a device body 502 that has a substantially flat surface area for contacting a surface area of foetal tissue and an opposite surface area for engaging with a doctor's or midwife's finger. In this particular example, the device body 502 has a size that is in the order of an adult's fingertip and is typically connected to an actuator for anchoring the device body 502 to the foetal tissue. In this particular embodiment, the device 500 comprises a first actuator 520 and a second actuator 522 as will be described in further detail below.

In this example, the device body 502 comprises a structure 504 to identify the surface area for engaging with the doctor's or midwife's finder and thereby also identifying the opposite surface area to be contacted to the foetal tissue. This may be advantageous as to reduce the risk of anchoring the device body 502 to the doctor's or midwife's finger. A person skilled in the art will appreciate that the device body 502 may alternatively comprise a pattern or the like to identify one of the opposite surface areas.

In a further embodiment (not shown), the device body 502 may comprise an attachment structure for removably attaching the device body 502 to the doctor's or midwife's fingertip. Such attachment structure may improve the process of guiding and placing the device body 502 against the foetal tissue. The structure may, for example, be in the form of a strap, a loop or a flange.

Referring back to the example shown in FIGS. 9 and 10, the device 500 further comprises a first protrusion in the form of a first coiled needle 506, and a second protrusion in the form of a second coiled needle 508. The first coiled needle 506 forms a biosensor for electrochemically measuring a concentration of the analyte in the foetus. The biosensor comprises a reactive substance that is selected to be reactive with the analyte in the foetal tissue and an electrode for detecting an electronic signal that is generated in response to the electrochemical reaction. Specifically, similar to the embodiment shown in FIGS. 3 to 5, the biosensor is in the form of a solid needle for example made of hardened Pt or Pt/Ir alloy that is coated or comprises the reactive substance. Non-exhaustive examples of reactive substances and electrochemical reactions are discussed above with reference to FIGS. 3 to 5. In this embodiment, the biosensor is configured to have properties similar to a medical needle in order to withstand forces that are applied when the first needle 506 is inserted into the foetal tissue, such as the foetal scalp.

The second coiled needle 508 forms a foetal electrode for detecting a heart rate of the foetus. A person skilled in the art will appreciate that foetal electrodes for detecting a heart rate are well known in the art and will not be described in further detail. An example of a well-known foetal electrode that can be inserted into foetal tissue relates to the Rocket Copeland Fetal Scalp Electrode. Whilst the exemplary device 500 comprises first and second coiled needles 506, 508, a person skilled in the art will appreciate that the device 500 may only comprise the first protrusion that forms the biosensor and that a separate device may be used to detect the heart rate of the foetus (if any).

The first and second coiled needles 506, 508 are further configured to form respective anchors for anchoring the device body 502 to the foetal tissue. Each needle 506, 508 is selectively movable between a passive configuration and an active configuration and vice versa by the use of respective actuators 520, 522 that are connected to the needles 506, 508 through wires 524, 526. However, a person skilled in the art will appreciate that both needles 506, 508 may be moved simultaneously by the use of a single actuator. Each or both of the wires 524, 526 may further be utilised to transmit the measured signal at the electrode of the biosensor for further analysis.

Figures 10A, 10B:
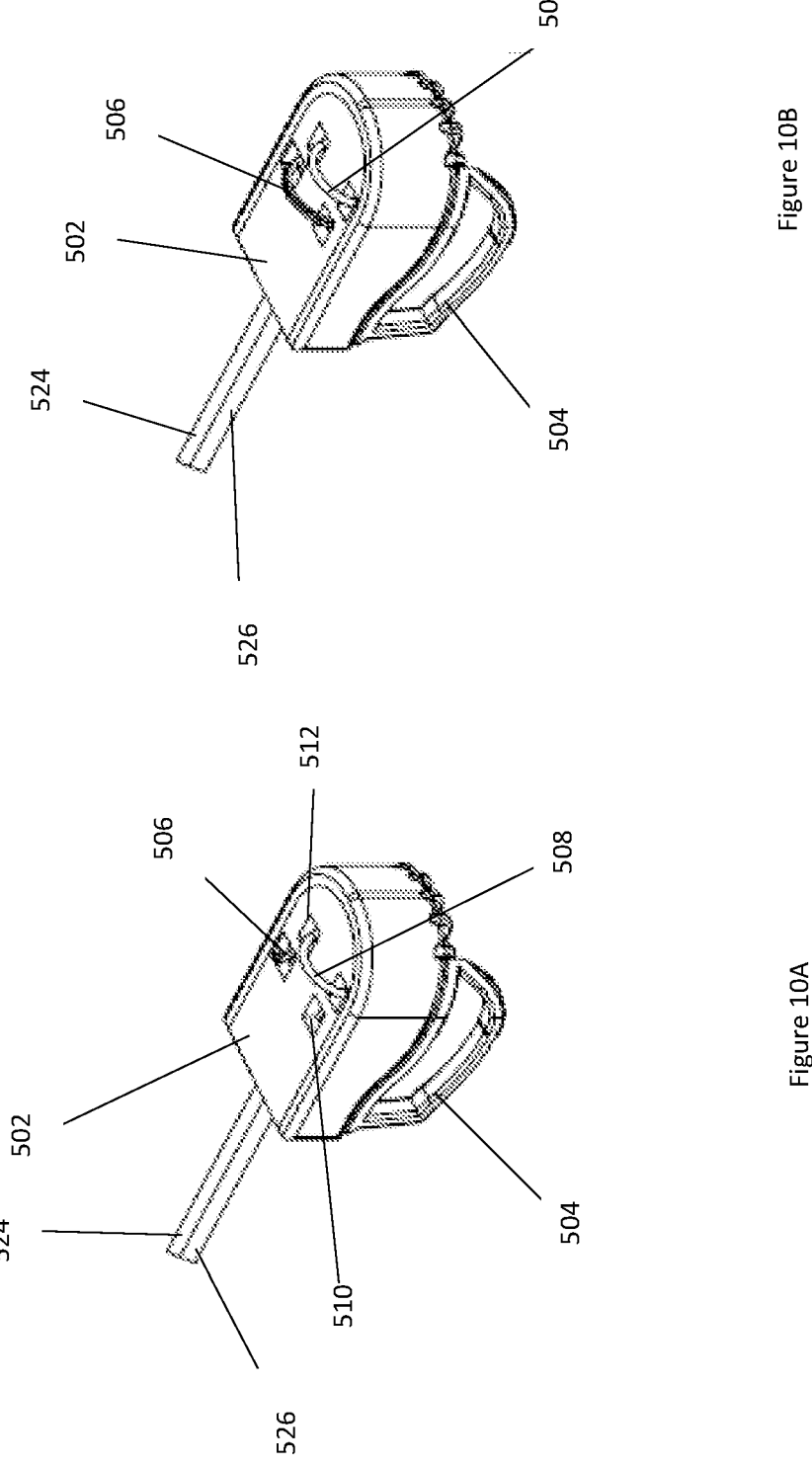
FIGS. 10A and 10B show different configurations of the device of FIG. 9.

The device body 502 comprises a first cavity 510 and a second cavity 512 that are arranged such that the first and second needles 506, 508 can be retracted and fully received within the respective cavities 510, 512 of the device body 502. FIG. 10A illustrates the device 500 wherein the first needle 506 is fully retracted and positioned within the first cavity 510 (passive configuration) and the second needle 508 is in the active configuration and forms a closed loop with the device body 502. FIG. 10B illustrates the device 500 when the first needle 506 has been moved from the passive configuration to the active configuration, also forming a closed loop with the device body 502. Thus, when the first and second needles 506, 508 are retracted into the respective cavities 510, 512, the needles/anchors 506, 508 are in the passive configuration and the device body 502 can be placed flush against the foetal tissue without inserting the first and second needles 506, 508 into the foetal tissue. The first and second needles 506, 508 are moveable from the passive configuration into the active configuration whereby sharp tips of the needles 506, 508 are inserted into the foetal tissue. Once the first and second needles 506, 508 are positioned in the active configuration, each of the first and second needles 506, 508 forms a closed loop with the device body 502 that encloses a portion of foetal tissue thereby anchoring the device body 502 to the foetal tissue.

In this particular example, each of the first and second needles 506, 508 is spring-loaded and the active configuration in which the first and second needles 506, 508 form closed loops with the device body 502 defines the default configuration. In other words, the actuators 520, 522 need to be operated to actively move the coiled first and second needles 506, 508 into the cavities 510, 512. In this way, the risk of unintentionally anchoring the device 500 may be reduced.

In an alternative embodiment (not shown), the reactive portion of the biosensor is located within a core portion of the needle. The needle may, for example, comprise a hollow space within which part of the biosensor is positioned. In this regard, the needle may comprise an opening in a side wall, such as a slit or a cut out, where the chemically reactive portion is exposed to an outer surface. In this way, once the needle is inserted into biological tissue, the exposed portion of the biosensor can electrochemically react with the analyte in the foetal tissue. This embodiment has the advantage that the needle itself can be composed of a mechanically strong material, such as stainless steel, without the need for a chemically reactive material composition. Even more so, the reactive portion of the biosensor may be made of a material that may not necessarily withstand the forces of inserting the device into the foetal tissue.

Figure 11:
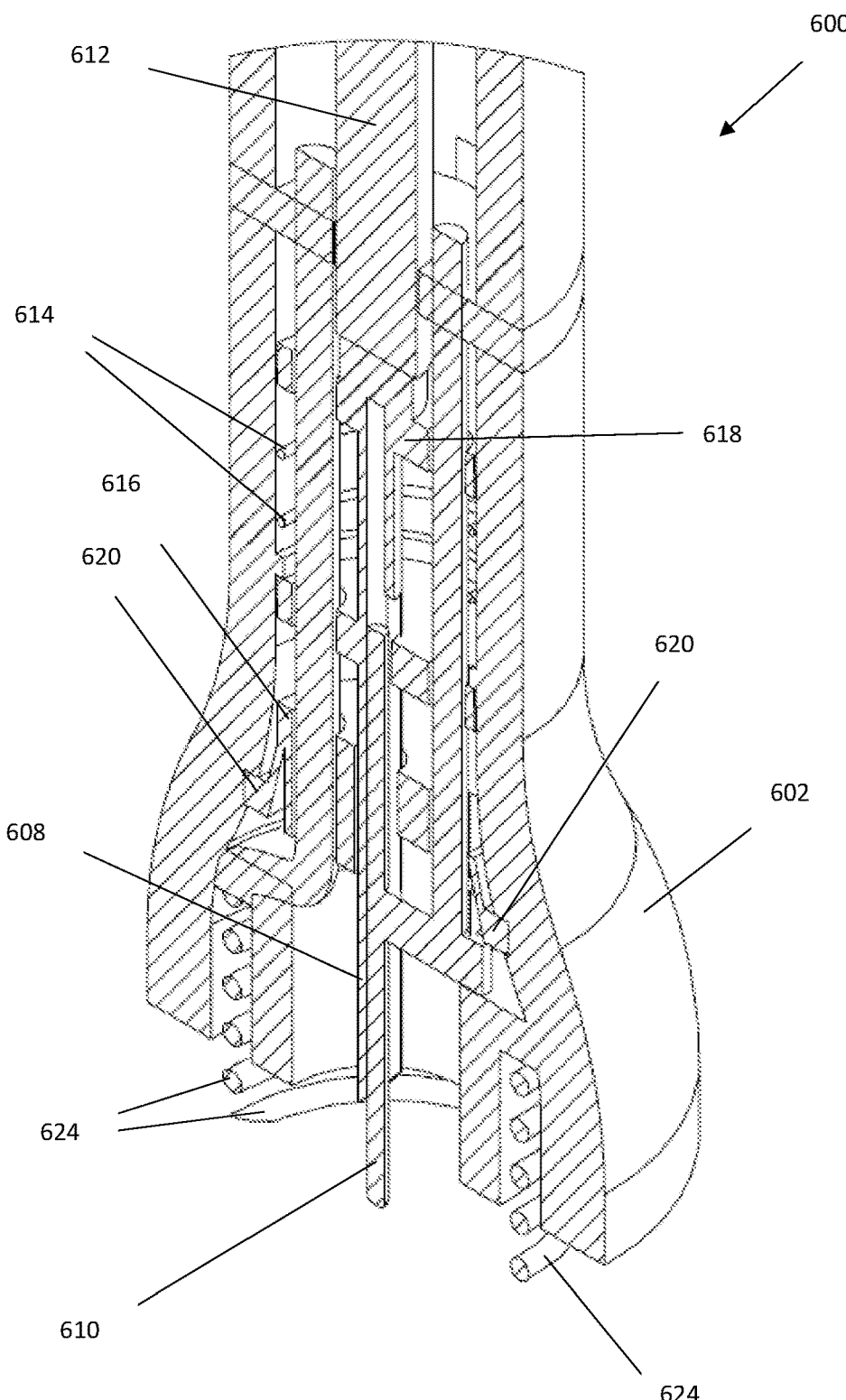
FIG. 11 shows a schematic representation of a device for monitoring a concentration of an analyte in a foetus in accordance with a further embodiment of the present invention.

Referring now to FIGS. 11 and 12, there is shown a device 600 for monitoring a concentration of an analyte in accordance with a further embodiment of the present invention. Similar to devices 300 and 500, the device 600 is configured to monitor a concentration of lactate in a foetus and may be the device 102 as part of the system 100 or system 200 shown in FIGS. 1 and 2. In this particular embodiment, a cannula configuration is used for implementing the device 600 as will be described in further detail below.

The device 600 comprises a device body 602 that has a shaft 604 for guiding the device 600 through the vaginal canal and the at least partially dilated cervix. The device 600 comprises a first needle 608 with a hollow tubular space, wherein the biosensor 610 is located within the tubular space of the needle 608. Similar to a cannula system, the first needle 608 is moveable relative to the biosensor 610 located within the hollow space in order to place a chemically reactive portion of the biosensor 610 into the foetal tissue while the needle 608 can be retracted. To illustrate this process in further detail, we now refer to FIGS. 12A to 12C that show different configurations of the device 600 for positioning the biosensor 610 in the foetal tissue. Referring initially to FIG. 12A, the needle 608 and biosensor 610 are shown in a passive, retracted configuration. In this configuration, the device 600 can be moved through the vaginal canal and the at least partially dilated cervix and positioned against a surface area of the foetal tissue. FIG. 12B shows the needle 608 and the biosensor 610 inserted into the foetal tissue and FIG. 12C illustrates the needle 608 being retracted while the biosensor 610 remains within the foetal tissue where the reactive substance of the biosensor 610 can react with the analyte of the tissue.

The device 600 further comprises an actuator for inserting the needle 608 together with the biosensor 610 into the foetal tissue. In this example, the actuator comprises a push button (not shown) provided at a distal end of the device 600, an internal shaft 612 connected to the push button, and a spring 614. When the actuator is operated by pressing the push button, the internal shaft 612 translates this movement and engages with a base portion 618 of the needle 608. In this way, the needle 608 together with the biosensor 610 are moved into the foetal tissue while the spring 614 of the actuator is compressed, as particularly shown in FIG. 12B.

Figure 12C:
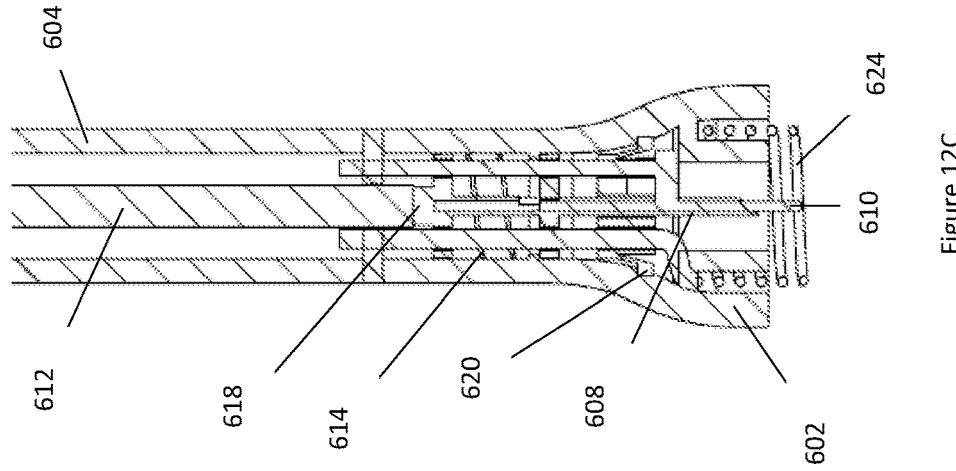
FIGS. 12A and 12B show different configurations of the device of FIG. 11.
Figure 12B:
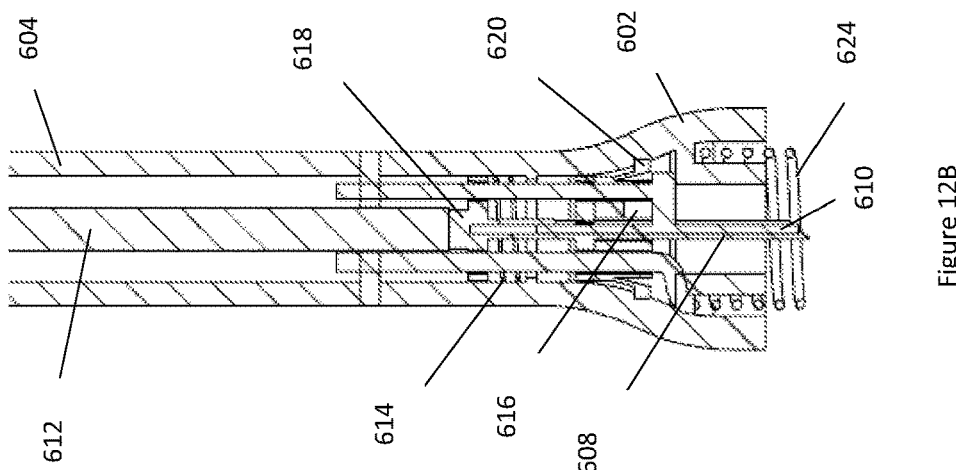
Figure 12A:
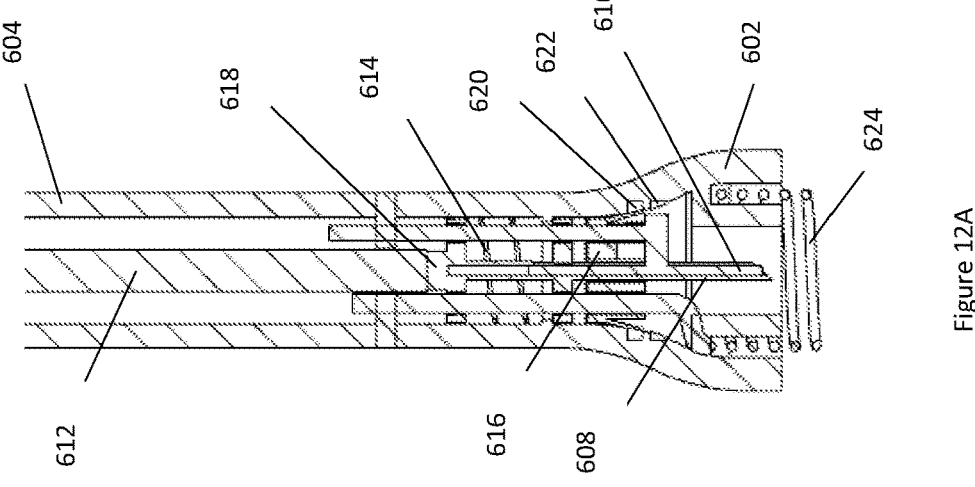

Once the push button of the actuator is released, the spring 614 expands and the needle 608 retracts into the housing of the device body 602, while the biosensor 610 remains within the foetal tissue as shown in particular in FIG. 12C. In order to lock the biosensor 610 in position within the foetal tissue, the device 600 further comprises a locking element 616. The locking component 616 has the function of locking the biosensor 610 in place once the biosensor 610 is positioned within the foetal tissue, while the needle 608 returns to its retracted configuration. The locking element 616 is connected to the biosensor 610 and is configured such that when the biosensor 610 has been inserted into the foetal tissue, a flange 620 of the locking element 616 engages with a receptacle 622 at an inner portion of the device body 602 thereby locking the biosensor in place, as particularly shown in FIGS. 12B and 12C.

The device 600 further comprises an anchor 624 for anchoring the device body 602 to the surface area of the biological tissue. The anchor 624 in this example forms a separate component from the needle 608. Specifically, the anchor 620 is in the form of a spiral that can be inserted into the foetal tissue by rotating the device body 602. In this example, the anchor 620 further functions as an electrode for detecting a heart rate of the foetus. Electrodes for detecting a heart rate of a foetus are well understood in the art and will therefore not be described in further detail. A person skilled in the art will appreciate that the anchor 624 of the device 600 may be shaped and sized in any suitable way. For example, instead of a spiral, the anchor 624 may be coiled and moveable from a passive to an active configuration, similar to the embodiment described with reference to FIGS. 9 and 10.

In a further embodiment (not shown), a device is provided with a similar configuration as device 600 shown in FIGS. 11 and 12. However, instead of a needle with a hollow, tubular space in which the biosensor is provided, the needle 608 forms the biosensor as, for example, described with reference to device 500 shown in FIGS. 9 and 10. In this particular embodiment, the actuator of the device may be simplified in that the spring 614 and the locking element 616 may not be necessary and the needle remains within the foetal tissue while monitoring the analyte of the foetus.

In a further embodiment (not shown), a device is provided with a similar configuration as device 600 shown in FIGS. 11 and 12. However, instead of the locking element 616, the biosensor 610 comprises a hook configured to anchor the biosensor within the foetal tissue. Thus, once the biosensor and the needle are inserted into the foetal tissue, the biosensor automatically hooks itself to the foetal tissue to remain in the foetal tissue while the needle retracts.

In a further embodiment (not shown), a device is provided with a similar configuration as device 500. However, the first needle is provided as a cannula system as described with reference to device 600. Specifically, the device comprises a substantially flat device body with cavities for receiving first and second needles that are coiled. The first and second needles are configured to selectively be moved between a passive configuration and an active configuration. In the passive configuration, the first and/or the second needle are retracted and fully received within the respective cavities of the device body. In the active configuration, the first and/or second needles form a closed loop with the surface area of the device body. When the device is anchored to biological tissue, the closed loop encloses a portion of biological tissue thereby anchoring the device to the biological tissue. With regard to the main difference to device 500, the first needle of this exemplary device comprises a hollow tubular space for accommodating the biosensor similar to the first needle of device 600. When the first needle is moved from the passive configuration to the active configuration, the first needle together with the biosensor are inserted into the biological tissue. The first needle is then retracted into the respective cavity of the device body while the a portion of the biosensor remains within the biological tissue in a coiled configuration.

Referring now to FIG. 14, there is shown a flowchart illustrating an exemplary method 700 of monitoring a concentration of an analyte in a foetus. The method 700 comprises a step 702 of providing a device for monitoring a concentration of an analyte in a foetus. The device may, for example, be device 300, 500 or 600 as shown in the accompanying drawings. The device comprises a protrusion, such as a needle, for being at least partially inserted into foetal tissue, such as a foetal scalp. The device further comprises a device body for contacting a surface area of the foetal tissue. In a further step 704, the protrusion is inserted at least partially into the foetal tissue, wherein the protrusion is part of a biosensor with an electrode and a chemically reactive substance. The substance is typically selected to be reactive with the analyte to be monitored. For example, if the analyte is lactate, the reactive substance may for example be lactate oxidase or lactate dehydrogenase. The method further comprises a step of anchoring the device body to the foetal tissue, for example, by moving 706 an anchor of the device from a passive configuration to an active configuration to insert anchoring elements of the anchor at least partially into the foetal tissue. A person skilled in the art will appreciate that the step of anchoring the device body may be performed before, after or at the same time as inserting the protrusion into the foetal tissue. The protrusion may, for example, be configured to form an anchor, such as a hook, a spiral or a clamp to anchor the device body to the foetal tissue. In a further step 708, an electronic signal is detected at the electrode of the biosensor, such as a current, wherein the electronic signal is indicative of the concentration of the analyte. The electronic signal is detected in response to an electrochemical reaction between the reactive substance of the biosensor and the analyte to be monitored in the foetus.

The device may comprise a guiding tube that protects the protrusion and the anchor from engaging with surrounding tissue when the device is guided through the vaginal canal and the cervix. As such, once the device is anchored to the foetal tissue, the guiding tube may be removed and only the wiring (if any) is kept in place connecting the device body with the external analysis component which reduces the discomfort for the mother.

The method may further comprise a step of removing the device body from the foetal tissue. In this regard, the anchor may be moved from the active configuration to the passive configuration which may automatically release the protrusion from the foetal tissue. However, it will be appreciated that the protrusion may be retractable and the method may comprise a step of retracting the protrusion before moving the anchoring elements.

The device may be used in combination with a Doppler ultrasound device which is routinely used to monitor progress of labour and maternal wellbeing and with an external CTG monitoring device to monitor the foetus' heartbeat. In situations where external monitoring poses difficulties or uncertainties, or where it results in abnormal patterns, the device for monitoring a concentration of an analyte may be used.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

What is claimed:

1. A device for monitoring a concentration of a lactate analyte in foetal tissue or foetal blood of a foetus, the device comprising:

a biosensor for continuously electrochemically measuring the concentration of the lactate analyte in the foetus, the biosensor comprising (A) a reactive substance on a working electrode and (B) a counter current electrode, wherein the reactive substance of the biosensor comprises an immobilised enzyme to react with the lactate analyte in the foetal tissue or foetal blood;

a protrusion in the form of a needle configured to be at least partially inserted into the foetal tissue, wherein the protrusion in the form of a needle comprises the reactive substance and functions as the working electrode of the biosensor;

an anchor, wherein the anchor forms a separate component to the protrusion in the form of the needle, wherein the anchor is in the form of a spiral;

wherein the anchor surrounds and is not in physical contact with the protrusion in the form of the needle on account of a gap located radially between the anchor and the protrusion in the form of a needle; and a device body supporting the biosensor comprising the protrusion in the form of the needle and the anchor, the device body being configured to contact a surface area of the foetal tissue, wherein the anchor anchors the device body to the foetal tissue by rotating the device body;

wherein the device is configured such that when the device body contacts the surface area of the foetal tissue, the device body can be anchored to the contacted surface area of the foetal tissue via the anchor and simultaneously the protrusion in the form of the needle comprising the reactive substance can be at least partially inserted into the foetal tissue so that the reactive substance of the biosensor electrochemically reacts with the lactate analyte in the foetal tissue or foetal blood and in response to the electrochemical reaction at a surface of the protrusion in the form of the needle in its function as the working electrode the biosensor detects an electronic signal, a strength of the electronic signal being indicative of the concentration of the lactate analyte or a rate of change of concentration of the lactate analyte in the foetal tissue or foetal blood; and wherein the device is configured to monitor the concentration of the lactate analyte or the rate of the change in the concentration of the lactate analyte continuously and in real-time.

2. The device of claim 1, comprising a foetal heart rate electrode for detecting a heart rate of the foetus.

3. The device of claim 2, wherein the device comprises a further protrusion configured to be inserted into the foetal tissue, wherein the further protrusion forms part of the foetal heart rate electrode for detecting the heart rate of the foetus.

4. The device of claim 1, wherein the immobilised enzyme is lactate oxidase or lactate dehydrogenase for detection of lactate in the foetal tissue and/or foetal blood.

5. The device of claim 1, further comprising a guiding tube for guiding the device body to the foetal tissue via a vaginal canal and a cervix.

6. The device of claim 1, wherein an outer surface area of the protrusion in the form of the needle is coated with the reactive substance of the biosensor.

7. The device of claim 1, wherein the protrusion in the form of the needle comprises a hollow space and the reactive substance of the biosensor is at least partially located within the hollow space of the protrusion in the form of a needle, wherein the protrusion in the form of the needle comprises an opening to the hollow space to expose the active substance of the biosensor to an outer surface of the protrusion in the form of the needle such that when the needle is inserted into the tissue, the reactive substance of the working electrode of the biosensor can electrochemically react with the lactate analyte in the foetal tissue at the opening.

8. A system for monitoring a concentration of a lactate analyte in foetal tissue or foetal blood of a foetus, the system comprising:

a) a device for continuously electrochemically measuring the concentration of the lactate analyte in the foetus, the device comprising:

i. a biosensor for electrochemically measuring a concentration of a lactate analyte in the foetus, the biosensor comprising (A) a reactive substance on a working electrode, and (B) a counter current electrode, wherein the reactive substance of the biosensor comprises an immobilised enzyme to react with the analyte in the foetal tissue or foetal blood;

ii. a protrusion in the form of a needle configured to be at least partially inserted into the foetal tissue, wherein the protrusion in the form of the needle comprises the reactive substance and functions as the working electrode of the biosensor;

iii. an anchor for anchoring the device body to the foetal tissue, wherein the anchor forms a separate component to the protrusion in the form of the needle, wherein the anchor is in the form of a spiral; wherein the anchor surrounds and is not in physical contact with the protrusion in the form of the needle on account of a gap located radially between the anchor and the protrusion in the form of a needle; and iv. a device body supporting the biosensor comprising the protrusion in the form of the needle and the anchor, the device body being configured to contact a surface area of the foetal tissue;

b) an analysis component in electronic communication with the working electrode and the counter current electrode of the biosensor, the analysis component being configured to determine information indicative of the concentration of the analyte using the detected electronic signal of the biosensor, wherein the system is configured such that when the device body contacts the surface area of the foetal tissue, the device body can be anchored to the contacted surface area of the foetal tissue via the anchor by rotating the device body and simultaneously the protrusion in the form of the needle comprising the reactive substance can be at least partially inserted into the tissue so that the reactive substance of the biosensor electrochemically reacts with the lactate analyte in the foetal tissue or foetal blood and in response to the electrochemical reaction at a surface of the protrusion in the form of a needle in its function as the working electrode the biosensor detects an electronic signal, a strength of the electronic signal being indicative of the concentration of the lactate analyte or the rate of the change of the concentration of the lactate analyte in the foetal tissue or foetal blood; and wherein the system is configured to monitor the concentration of the lactate analyte or rate of change in concentration of the lactate analyte continuously and in real-time.

9. The system of claim 8, comprising an external housing for housing the analysis component, wherein the external housing comprises an attachment for attaching the external housing to a body part of the mother.

10. A method of monitoring a concentration of a lactate analyte in foetal tissue or foetal blood of a foetus, the method comprising:

a) providing a device for continuously electrochemically measuring the concentration of the lactate analyte in the foetus, the device comprising:

i. a biosensor for electrochemically measuring a concentration of a lactate analyte in the foetus, the biosensor comprising (A) a reactive substance on a working electrode, and (B) a counter current electrode, wherein the reactive substance of the biosensor comprises an immobilised enzyme to react with an analyte in the foetal tissue or foetal blood;

ii. a protrusion in the form of a needle configured to be at least partially inserted into the foetal tissue, wherein the protrusion in the form of the needle comprises the reactive substance and functions as the working electrode of the biosensor;

iii. an anchor, wherein the anchor forms a separate component to the protrusion in the form of the needle, wherein the anchor is in the form of a spiral; wherein the anchor surrounds and is not in physical contact with the protrusion in the form of a needle on account of a gap located radially between the anchor and the protrusion in the form of the needle; and iv. a device body supporting the biosensor comprising the protrusion in the form of the needle and the anchor, the device body being configured to contact a surface area of the foetal tissue; and b) anchoring the device to the foetal tissue with the anchor by rotating the device body and simultaneously inserting the protrusion in the form of the needle at least partially into the foetal tissue;

c) detecting an electronic signal at the working electrode of the biosensor, the electronic signal being in response to an electrochemical reaction between the reactive substance of the biosensor and the lactate analyte to be monitored;

wherein the method is conducted such that the detected electronic signal is indicative of the concentration of the lactate analyte or a rate of change of concentration of the lactate analyte in the foetal tissue or foetal blood; and wherein the method monitors the concentration of the lactate analyte or the of the change in concentration of the lactate analyte continuously and in real-time.

* * * * *